US010327855B2

United States Patent
Hourtash et al.

(10) Patent No.: US 10,327,855 B2
(45) Date of Patent: Jun. 25, 2019

(54) SYSTEMS AND METHODS FOR UTILIZING AUGMENTED JACOBIAN TO CONTROL MANIPULATOR JOINT MOVEMENT

(71) Applicant: Intuitive Surgical Operations, Inc., Sunnyvale, CA (US)

(72) Inventors: Arjang M. Hourtash, Santa Clara, CA (US); Nitish Swarup, Sunnyvale, CA (US); Pushkar Hingwe, Fremont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 165 days.

(21) Appl. No.: 15/512,495

(22) PCT Filed: Sep. 17, 2015

(86) PCT No.: PCT/US2015/050655
§ 371 (c)(1),
(2) Date: Mar. 17, 2017

(87) PCT Pub. No.: WO2016/044574
PCT Pub. Date: Mar. 24, 2016

(65) Prior Publication Data
US 2017/0273748 A1 Sep. 28, 2017

Related U.S. Application Data

(60) Provisional application No. 62/051,696, filed on Sep. 17, 2014.

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/74* (2016.02); *A61B 34/77* (2016.02); *B25J 9/1607* (2013.01);
(Continued)

(58) Field of Classification Search
CPC ......... A61B 34/30; A61B 34/35; A61B 34/74; A61B 34/77; B25J 9/1607; G05B 2219/45123
See application file for complete search history.

(56) References Cited

U.S. PATENT DOCUMENTS

| 4,893,254 A | 1/1990 | Chan et al. |
| 5,737,500 A | 4/1998 | Seraji et al. |

(Continued)

FOREIGN PATENT DOCUMENTS

| EP | 2332484 A2 | 6/2011 |
| WO | WO-2006124390 A2 | 11/2006 |

(Continued)

OTHER PUBLICATIONS

International Search Report and Written Opinion for Application No. PCT/US15/50655, dated Dec. 21, 2015, 18 pages.

(Continued)

*Primary Examiner* — Khoi H Tran
*Assistant Examiner* — Robert T Nguyen
(74) *Attorney, Agent, or Firm* — Ferguson Braswell Fraser Kubasta PC

(57) ABSTRACT

Devices, systems, and methods for providing commanded movement of an end effector of a manipulator while providing a desired movement of one or more joints of the manipulator. Methods include augmenting a Jacobian so that joint movements calculated from the Jacobian perform one or more auxiliary tasks and/or desired joint movements concurrent with commanded end effector movement, the one
(Continued)

or more auxiliary tasks and/or desired joint movements extending into a null-space. The auxiliary tasks and desired joint movements include inhibiting movement of one or more joints, inhibiting collisions between adjacent manipulators or between a manipulator and a patient surface, commanded reconfiguration of one or more joints, or various other tasks or combinations thereof. Such joint movements may be provided using joint velocities calculated from the pseudo-inverse solution of the augmented Jacobian. Various configurations for systems utilizing such methods are provided herein.

31 Claims, 29 Drawing Sheets

(51) Int. Cl.
*A61B 34/35* (2016.01)
*B25J 9/16* (2006.01)
(52) U.S. Cl.
CPC .... *A61B 34/35* (2016.02); *G05B 2219/45123* (2013.01)

(56) References Cited

U.S. PATENT DOCUMENTS

| | | | |
|---|---|---|---|
| 8,620,473 B2 | 12/2013 | Diolaiti et al. | |
| 2007/0013336 A1* | 1/2007 | Nowlin | B25J 9/1682 318/568.21 |
| 2010/0331855 A1* | 12/2010 | Zhao | A61B 34/30 606/130 |
| 2010/0332033 A1 | 12/2010 | Diolaiti et al. | |
| 2012/0245736 A1 | 9/2012 | Bosscher et al. | |
| 2013/0325030 A1 | 12/2013 | Hourtash et al. | |
| 2014/0276953 A1* | 9/2014 | Swarup | B25J 18/007 606/130 |
| 2014/0276954 A1* | 9/2014 | Hourtash | B25J 9/1607 606/130 |
| 2014/0316430 A1* | 10/2014 | Hourtash | B25J 9/1607 606/130 |
| 2014/0316431 A1* | 10/2014 | Hourtash | B25J 9/1607 606/130 |
| 2017/0095301 A1* | 4/2017 | Brisson | A61B 34/35 |

FOREIGN PATENT DOCUMENTS

| | | |
|---|---|---|
| WO | WO-2009055707 A1 | 4/2009 |
| WO | WO-2013181503 A1 | 12/2013 |
| WO | WO-2013181507 A1 | 12/2013 |
| WO | WO-2014146119 A1 | 9/2014 |
| WO | WO-2014146120 A1 | 9/2014 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Baerlocher, P. et al., "Task Priority Formulations for the Kinematic Control of Highly Redundant Articulated Structures," IEEE/RSJ International Conference on Intelligent Robots and Systems, 1998, pp. 323-329, vol. 1, IEEE.

Funda, Janez et al., "Constrained Cartesian Motion Control for Teleoperated Surgical Robots," IEEE Transactions on Robotics and Automation, IEEE, Jun. 1996, vol. 12, No. 3, pp. 453-465.

Jamshidi et al., "Robotics and Manufacturing—Recent Trends in Research, Education and Applications," Proceedings of the Second International Symposium of Robotics and Manufacturing: Research, Education, and Applications, ASME Press, Nov. 16-18, 1988, 17 pages.

Maciejewski A.A., et al., "Obstacle Avoidance for Kinematically Redundant Manipulators in Dynamically Varying Environments," International Journal of Robotics Research, 1985, vol. 4 (3), pp. 109-116.

Extended European Search Report for Application No. EP15842454.9, dated Apr. 11, 2018, 9 pages.

\* cited by examiner

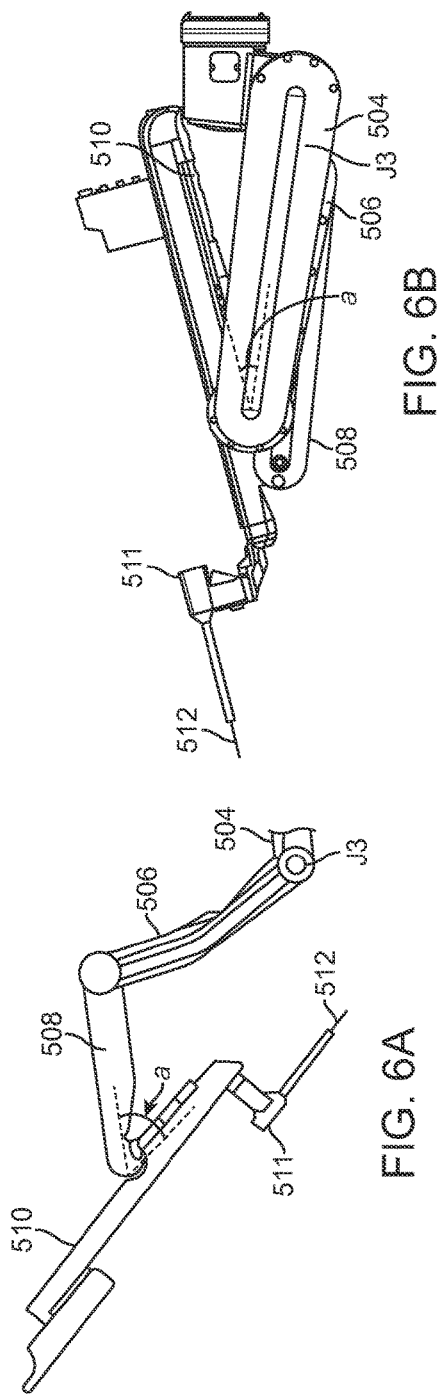
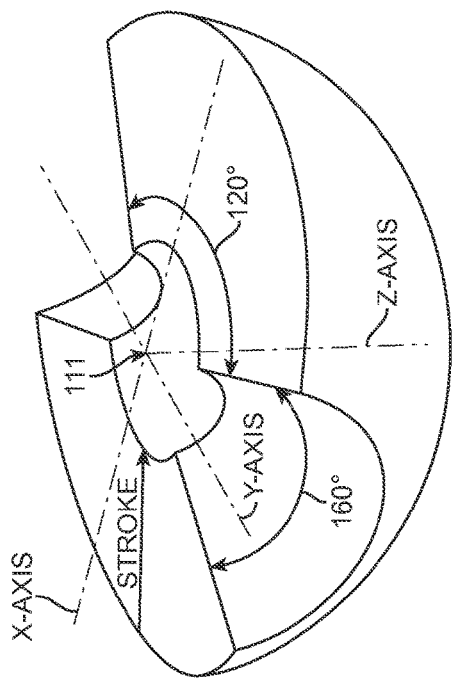
FIG. 6A
FIG. 6B
FIG. 6C

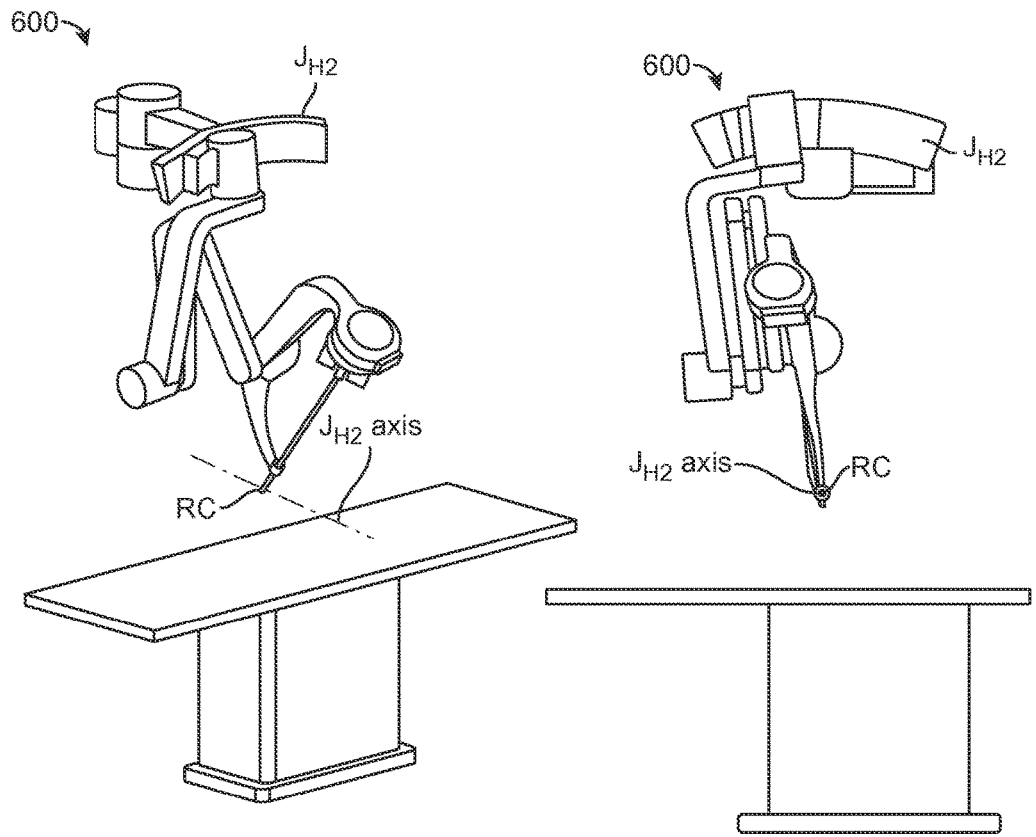
FIG. 13A
FIG. 13B
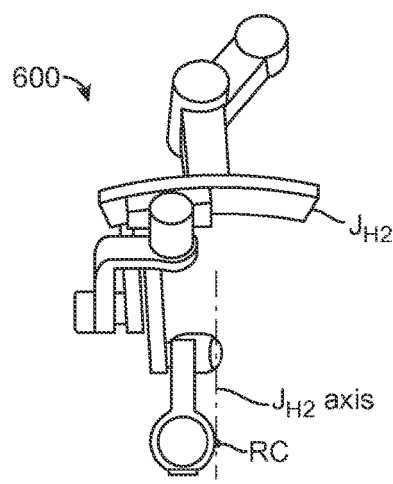
FIG. 13C $\theta_2 > \theta_1$

SYSTEMS AND METHODS FOR UTILIZING AUGMENTED JACOBIAN TO CONTROL MANIPULATOR JOINT MOVEMENT

RELATED APPLICATIONS

This patent application is a U.S. National Stage Filing under 35 U.S.C. 371 from International Application No. PCT/US2015/050655, filed on Sep. 17, 2015, and published as WO 2016/044574 A1 on Mar. 24, 2016, which claims priority to and the benefit of the filing date of U.S. Provisional Patent Application 62/051,696, entitled "SYSTEMS AND METHODS UTILIZING AUGMENTED JACOBIAN TO CONTROL MANIPULATOR JOINT MOVEMENT," filed Sep. 17, 2014, each of which is incorporated by reference herein in its entirety.

CROSS-REFERENCES TO RELATED APPLICATIONS

The present application is generally related to the following commonly-owned applications: U.S. application Ser. No. 12/494,695 filed Jun. 30, 2009, entitled "Control of Medical Robotic System Manipulator About Kinematic Singularities;" U.S. application Ser. No. 12/406,004 filed Mar. 17, 2009, entitled "Master Controller Having Redundant Degrees of Freedom and Added Forces to Create Internal Motion;" U.S. application Ser. No. 11/133,423 filed May 19, 2005 (U.S. Pat. No. 8,004,229), entitled "Software Center and Highly Configurable Robotic Systems for Surgery and Other Uses;" U.S. application Ser. No. 10/957,077 filed Sep. 30, 2004 (U.S. Pat. No. 7,594,912), entitled "Offset Remote Center Manipulator For Robotic Surgery;" and U.S. application Ser. No. 09/398,507 filed Sep. 17, 1999 (U.S. Pat. No. 6,714,839), entitled "Master Having Redundant Degrees of Freedom;" U.S. application Ser. No. 13/967,606, entitled "Systems and Methods for Cancellation of Joint Motion Using the Null-Space," filed Aug. 15, 2013; U.S. application Ser. No. 13/906,713, entitled "Manipulator Arm-to-Patient Collision Avoidance Using a Null-Space," filed May 31, 2013; U.S. application Ser. No. 13/906,767, entitled "Systems and Methods for Commanded Reconfiguration of a Surgical Manipulator Using the Null-Space," filed May 31, 2013; U.S. application Ser. No. 13/906,819, entitled "Systems and Methods for Avoiding Collisions Between Manipulator Arms Using a Null-Space," filed May 31, 2013; and U.S. application Ser. No. 14/218,788, entitled "System and Methods for Positioning a Manipulator Arm by Clutching Within a Null-Perpendicular Space Concurrent with Null-Space Movement," filed Mar. 18, 2014; U.S. application Ser. No. 14/218,871, entitled "Systems and Methods for Facilitating Access to Edges of Cartesian-Coordinate Space Using the Null Space," filed Mar. 18, 2014; U.S. application Ser. No. 14/218,862, entitled "Systems and Methods for Tracking a Path Using the Null-Space," filed Mar. 18, 2014; and U.S. application Ser. No. 14/218,842, entitled "Systems and Methods for Using the Null Space to Emphasize Manipulator Joint Motion Anisotropically," filed Mar. 18, 2014; the disclosures of which are incorporated herein by reference in their entireties.

BACKGROUND OF THE INVENTION

The present invention generally provides improved surgical and/or robotic devices, systems, and methods.

Minimally invasive medical techniques are aimed at reducing the amount of tissue which is damaged during diagnostic or surgical procedures, thereby reducing patient recovery time, discomfort, and deleterious side effects. Millions of "open" or traditional surgeries are performed each year in the United States; many of these surgeries can potentially be performed in a minimally invasive manner. However, only a relatively small number of surgeries currently use minimally invasive techniques due to limitations in surgical instruments, and techniques, and the additional surgical training required to master them.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn controls the motion of robotic instruments. The robotic surgical instruments can be inserted through small, minimally invasive surgical apertures to treat tissues at surgical sites within the patient, often avoiding the trauma associated with accessing for open surgery. These robotic systems can move the working ends of the surgical instruments with sufficient dexterity to perform quite intricate surgical tasks, such as by pivoting shafts of the instruments at the minimally invasive aperture, sliding of the shaft axially through the aperture, rotating of the shaft within the aperture, and/or the like.

The servomechanism used for telesurgery will often accept input from two master controllers (one for each of the surgeon's hands) and may include two or more robotic arms or manipulators. Mapping of the hand movements to the image of the robotic instruments displayed by the image capture device can help provide the surgeon with accurate control over the instruments associated with each hand. In many surgical robotic systems, one or more additional robotic manipulator arms are included for moving an endoscope or other image capture device, additional surgical instruments, or the like.

A variety of structural arrangements can be used to support the surgical instrument at the surgical site during robotic surgery. The driven linkage or "slave" is often called a robotic surgical manipulator, and example as a robotic surgical manipulator during minimally invasive robotic surgery are described in U.S. Pat. Nos. 6,758,843; 6,246,200; and 5,800,423, the full disclosures of which are incorporated herein by reference. These linkages often make use of a parallelogram arrangement to hold an instrument having a shaft. Such a manipulator structure can constrain movement of the instrument so that the instrument shaft pivots about a remote center of spherical rotation positioned in space along the length of the rigid shaft. By aligning this center of rotation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 6,702,805; 6,676,669; 5,855, 583; 5,808,665; 5,445,166; and 5,184,601, the full disclosures of which are incorporated herein by reference.

While the new robotic surgical systems and devices have proven highly effective and advantageous, still further improvements would be desirable. For example, a manipulator arm may include additional redundant joints to provide increased movements or configurations under certain conditions. When moving surgical instruments within a minimally invasive surgical site, however, these joints may exhibit a significant amount of movement outside the patient, often more movement than needed or expected, particularly when pivoting instruments about minimally invasive apertures through large angular ranges. Alternative manipulator structures have been proposed which employ software control over joints of a highly configurable kinematic manipulator to restrain pivotal motion at the insertion site while inhibiting inadvertent manipulator/manipulator contact outside the patient (or the like). These highly configurable "software center" surgical manipulator systems may provide significant advantages, but may also present challenges. In particular, the mechanically constrained remote-center linkages may offer safety advantages in some conditions. Additionally, the wide range of configurations of the numerous joints often included in these manipulators may result in the manipulators being difficult to manually set-up in a configuration that is desirable for a particular procedure. As the range of surgeries being performed using tele-surgical systems continues to expand, there is an increasing demand for expanding the available configurations and the range of motion of the instruments within the patient. Unfortunately, both of these changes can increase the challenges associated with the motion of the manipulators outside the body, and further increase the importance of avoiding unnecessary movement of the manipulators arm for certain tasks or to provide improved movement so as to avoid undesired contact between manipulators or between external portions of the manipulator and the patient.

For these and other reasons, it would be advantageous to provide improved devices, systems, and methods for surgery, robotic surgery, and other robotic applications. It would be beneficial if these improved technologies provided the ability to limit the amount of movement of the manipulator arm during certain tasks. It would be particularly beneficial if these improved technologies provided the ability to avoid collisions between the manipulator arm and the patient while maintaining a desired end effector state or a desired location of a remote center about which the instrument shaft pivots. Ideally, these improvements would allow for improved movement of one or more manipulator arms during a surgical procedure while avoiding collisions between the manipulator arms and the patient during end effector movement. Additionally, it would be desirable to provide such improvements while increasing the range of motion of the instruments for at least some procedures and without significantly increasing the size, mechanical complexity, or costs of these systems, and while maintaining or improving their dexterity.

BRIEF SUMMARY OF THE INVENTION

The present invention generally provides improved robotic and/or surgical devices, systems, and methods. In many embodiments, the invention will employ highly configurable surgical robotic manipulators. These manipulators, for example, may have more degrees of freedom of movement than the associated surgical end effectors have within a surgical workspace. A robotic surgical system in accordance with the present invention typically includes a manipulator arm supporting a robotic surgical instrument and a processor to calculate coordinated joint movements for manipulating an end effector of the instrument. The joints of the robotic manipulators supporting the end effectors allow the manipulator to move throughout a range of different configurations for a given end effector position and/or a given pivot point location. A manipulator may include additional redundant joints to allow for various types of auxiliary movements, such as a reconfiguration movement in response to a user command or another type of movement, such as a collision avoidance movement. Such movements may be provided while maintaining a given state of the end effector in a number of ways. In certain embodiments, such movements are provided by augmenting a Jacobian of the manipulator so that joint velocities obtained by calculating a pseudo-inverse of the augmented Jacobian provide the desired auxiliary movements or desired movements of the manipulator in addition to, often concurrent with, commanded end effector movement.

In another aspect, any of the methods described herein may include: determining one or more auxiliary movements of the plurality of joints using the calculated joint velocities, and driving the joints according to the calculated auxiliary movement while maintaining a desired state of the end effector. The one or more auxiliary movements may include a desired movement of a second set of joints of the plurality of joints. The second set of joints may include one or more joints that may include one or more joints within the first set of joints. The one or more auxiliary movement may include: a commanded reconfiguration movement, a collision avoidance movement, an auxiliary task, or any combination thereof.

In one aspect of the present invention, a redundant degrees of freedom (RDOF) surgical robotic system with manipulation input is provided. The RDOF surgical robotic system comprises a manipulator assembly, one or more user input devices, and a processor with a controller. A manipulator arm of the assembly has a plurality of joints providing sufficient degrees of freedom that allow a range of joint states for a given end effector state. Typically, in response to receiving a manipulation command to move the end effector with a desired movement, the system calculates joint velocities by calculating a pseudo-inverse of a Jacobian of the manipulator and drives the joints according to the calculated movements to effect the desired end effector movement. By augmenting the Jacobian, various the calculated joint movements can provide various other auxiliary tasks or desired movements within a null-space. To enlarge the manipulator's work space or to allow various auxiliary tasks, some embodiments of the system include a revolute proximal most joint of the manipulator arm and/or a distal revolute joint coupling an instrument to a proximal portion of the manipulator arm.

In one aspect, the proximal portion of the manipulator arm is attached to the base such that movement of the proximal portion relative to the base is inhibited while the joints are driven. In another aspect, the proximal portion is coupled to the base by a joint such that the proximal portion of the manipulator arm is moveable relative to the base while the joints are driven. In an example embodiment, the joint coupling the proximal portion of the manipulator to the base is a revolute joint that supports the manipulator arm such that joint movement of the revolute joint pivots one or more joints of the manipulator arm about a pivotal axis of the revolute joints. In many embodiments, the pivotal axis of the revolute joint extends from the joints through a remote center about which an instrument shaft of the end effector pivots. In one aspect, movement of the revolute joint pivots one or more joints of the manipulator arm about a cone distally tapered and oriented towards the distal end effector, typically the remote center. The cone around which the manipulator arm pivots in this aspect, corresponds to a cone shaped void within the range of motion of the tool tip, in which the movement of the tool may be impossible or impaired, discussed in further detail below.

In another aspect, the joint coupling the proximal portion of the manipulator to the base is moveable relative to the base along a path, typically an arcuate or substantially circular path such that movement of the joint along the path pivots one or more joints of the manipulator arm about an axis extending through a distal portion of the manipulator arm near the instrument, preferably through a remote center about which the instrument shaft pivots. In some embodiments, the manipulator includes a revolute joint coupling the proximal portion of the manipulator to the base, the revolute joint being moveable relative to the base along a path, which may linear, arcuate or substantially circular.

In another aspect of the present invention, the manipulator is configured to move such that an intermediate portion of the instrument shaft pivots about a remote center. Between the manipulator and the instrument, there are a plurality of driven joints providing sufficient degrees of freedom to allow a range of joint states for an end effector position when the intermediate portion of the instrument shaft extends through an access site. A processor having a controller couples the input device to the manipulator. In response to a reconfiguration command, the processor determines movements of one or more joints to effect the desired reconfiguration so that the intermediate portion of the instrument is within the access site during the end effector's desired movement and maintains the desired remote center location about which the shaft pivots. In certain embodiments, in response to receiving a manipulation command to effect a desired end effector's movement, the system determines calculated movements that achieve the desired end effector movement by calculating a pseudo-inverse of a Jacobian that is augmented so that the instrument shaft pivots about the remote center.

In certain embodiments, the movement of the joints are calculated by use of a Jacobian that is augmented so as to avoid driving a first set of joints of the plurality such that either the first set of joints are effectively locked out, or so that the first set of joints are not driven to effect the end effector displacing movement. The first set of joints may include one or more joints of the manipulator arm. The Jacobian may be augmented so that a reconfiguration movement of the first set of joints is calculated so that movement of a joint from the first set of joints provides a substantially constant speed of the joint for a duration of the reconfiguration. In some embodiments, a joint from the first set of joints of the manipulator is a revolute joint coupling the manipulator arm to the base. The desired state of the end effector may include a desired position, velocity or acceleration of the end effector. Generally, the manipulation command and the reconfiguration command are separate inputs, typically being received from separate users on separate input device, or these separate inputs may be received from the same user. In some embodiments, the end effector manipulation command is received from an input device by a first user, such as a surgeon entering the command on a surgical console master input, while the reconfiguration command is received from an input device by a second user on a separate input device, such as a physician's assistant entering the reconfiguration command on a patient side cart input device. In other embodiments, the end effector manipulation command and the reconfiguration command are both received by the same user from input devices at a surgical console. In other embodiments, the end effector manipulation command and the reconfiguration command are both received by the same user from input devices at a patient side cart.

A further understanding of the nature and advantages of the present invention will become apparent by reference to the remaining portions of the specification and drawings.

BRIEF DESCRIPTION OF THE DRAWINGS

FIGS. 6A-6B show an example manipulator arm in the pitch forward configuration and pitch back configurations, respectively.

FIG. 6C shows a graphical representation of the range of motion of the surgical instrument tool tip of an example manipulator arm, including a cone of silence or conical tool access limit zone in each of the pitch forward and pitch back configurations.

FIGS. 12A-13C show exemplary manipulator arms having a proximal joint that translates a proximal joint supporting the manipulator arm about a path of the joint.

DETAILED DESCRIPTION OF THE INVENTION

Figure 1A:
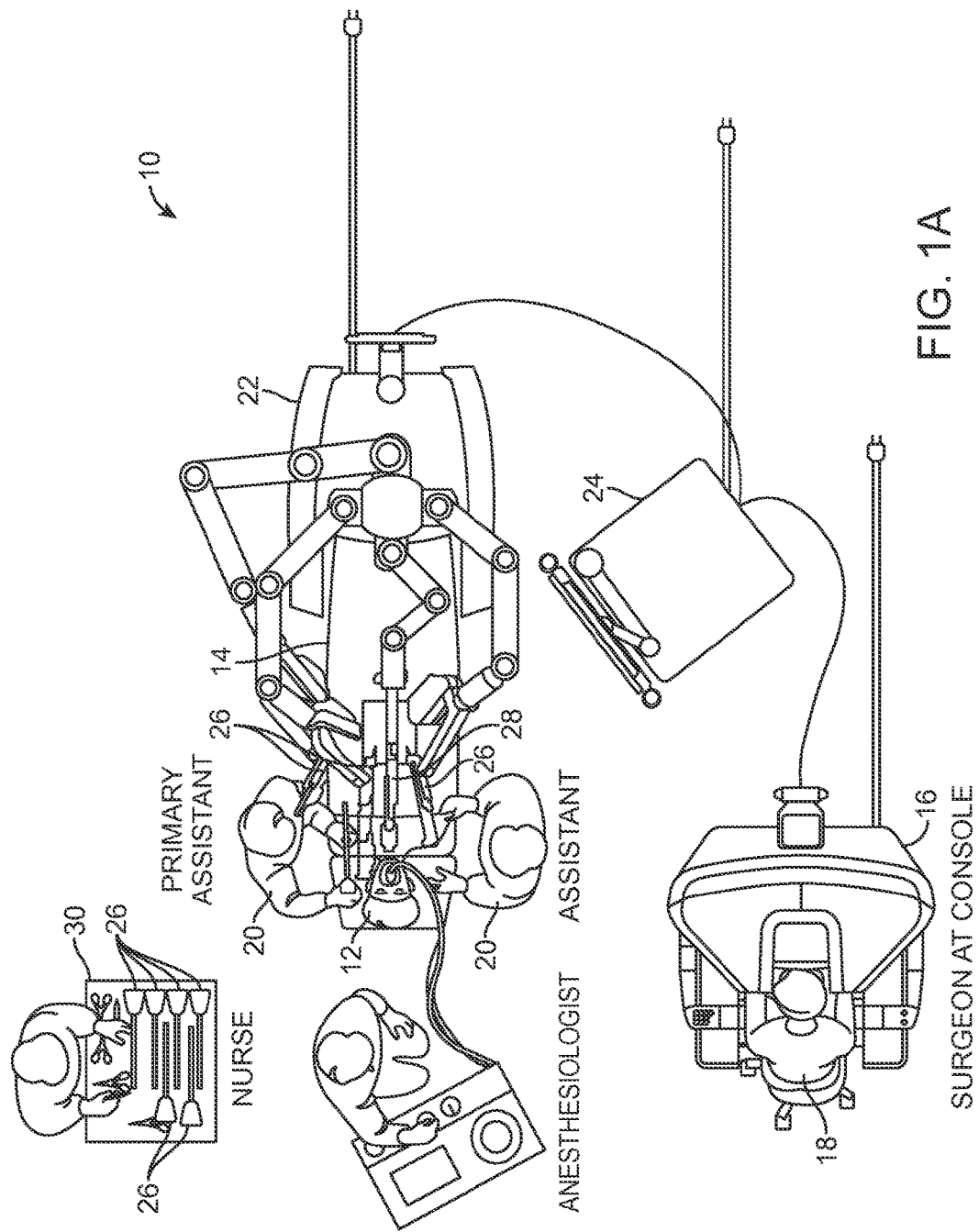
FIG. 1A is an overhead view of a robotic surgical system in accordance with embodiments of the present invention, the robotic surgical system having a surgical station with a plurality of robotic manipulators for robotically moving surgical instruments having surgical end effectors at an internal surgical site within a patient.

The present invention generally provides improved surgical and robotic devices, systems, and methods. The invention is particularly advantageous for use with surgical robotic systems in which a plurality of surgical tools or instruments will be mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site. While aspects of the invention are generally described manipulators having redundant degrees of freedom, it is appreciated that aspects may apply to non-redundant manipulators, for example a manipulator experiencing or approaching a singularity.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector which is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base which is fixed in space during at least a portion of a robotic procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both. When used for minimally invasive robotic surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site into a surgical workspace, rotation of the shaft about its axis, and pivotal motion of the shaft about a pivot point adjacent the access site.

Many of the example manipulator assemblies described herein have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation—plus three degrees of freedom to comply with the access site constraints), but will often have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly within the null-space of the Jacobian.

The invention provides robotic linkage structures which are particularly well suited for surgical (and other) applications in which a wide range of motion is desired, and for which a limited dedicated volume is available due to the presence of other robotic linkages, surgical personnel and equipment, and the like. The large range of motion and reduced volume needed for each robotic linkage may also provide greater flexibility between the location of the robotic support structure and the surgical or other workspace, thereby facilitating and expediting setup.

The term "state" of a joint or the like will often herein refer to the control variables associated with the joint. For example, the state of an angular joint can refer to the angle defined by that joint within its range of motion, and/or to the angular velocity of the joint. Similarly, the state of an axial or prismatic joint may refer to the joint's axial position, and/or to its axial velocity. While many of the controllers described herein comprise velocity controllers, they often also have some position control aspects. Alternative embodiments may rely primarily or entirely on position controllers, acceleration controllers, or the like. Many aspects of control system that can be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, and/or the like.

In certain aspects, the tool of an exemplary manipulator arm pivots about a pivot point adjacent a minimally invasive aperture. In some embodiments, the system may utilize a hardware remote center, such as the remote center kinematics described in U.S. Pat. No. 6,786,896, the entire contents of which are incorporated herein by reference. Such systems may utilize a double parallelogram linkage which constrains the movement of the linkages such that the shaft of the instrument supported by the manipulator pivots about a remote center point. Alternative mechanically constrained remote center linkage systems are known and/or may be developed in the future. Surprisingly, work in connection with the present invention indicates that remote center linkage systems may benefit from highly configurable kinematic architectures. In particular when a surgical robotic system has a linkage that allows pivotal motion about two axes intersecting at or near a minimally invasive surgical access site, the spherical pivotal motion may encompass the full extent of a desired range of motion within the patient, but may still suffer from avoidable deficiencies (such as being poorly conditioned, being susceptible to arm-to-arm or arm-to-patient contact outside the patient, and/or the like). At first, adding one or more additional degrees of freedom that are also mechanically constrained to pivotal motion at or near the access site may appear to offer few or any improvements in the range of motion. Nonetheless, surprisingly, such joints can provide significant advantages by allowing the overall system to be configured in or driven toward a collision-inhibiting pose, by further extending the range of motion for other surgical procedures, and the like. In other embodiments, the system may utilize software to achieve a remote center, such as described in U.S. Pat. No. 8,004,229, the entire contents of which are incorporated herein by reference. In a system having a software remote center, the processor calculates movement of the joints so as to pivot an intermediate portion of the instrument shaft about a pivot point determined, as opposed to a mechanical constraint. By having the capability to compute software pivot points, different modes characterized by the compliance or stiffness of the system can be selectively implemented. More particularly, different system modes over a range of pivot points/centers (e.g., moveable pivot points, passive pivot points, fixed/rigid pivot point, soft pivot points) can be implemented as desired.

Despite the many advantages of a robotic surgical system having multiple highly configurable manipulators, since the manipulators include a relatively large number of joints and links between the base and instrument, manual positioning of the links can be challenging and complicated. Even when the manipulator structure is balanced so as to avoid gravitational effects, attempting to align each of the joints in an appropriate arrangement or to reconfigure the manipulator as desired can be difficult, time consuming, and may involve significant training and/or skill. The challenges can be even greater when the links of the manipulator are not balanced about the joints, such that positioning such a highly configurable structures in an appropriate configuration before or during surgery can be a struggle due to the manipulator arm length and the passive and limp design in many surgical systems.

These issues can be addressed by allowing a user, such as a physician's assistant, to quickly and easily reconfigure the manipulator arm, while and maintaining the desired end effector state, optionally even during movement of the end effector during a surgical procedure. One or more additional joints may be included in the manipulator arm to increase the range of motion and configurations of the manipulator arm to enhance this capability. While providing additional joints may provide increased range of motion for certain tasks, the large number of redundant joints in the manipulator arm may cause various movements of the arm to be overly complex for other tasks, such that the movements appear unpredictable or the amount of overall movements causes various other clinical concerns. It may further be useful to cancel movement of the one or more joints for which no movement is desired for a first task (referred to herein as "locked" joints or a "locked set of joints") while allowing movement of the locked set of joints for various other tasks that may be performed concurrently with the first task. Locking out certain joints without actually physically constraining movement of the locked out joints is advantageous since movement of the locked out joints may be desired to effect other tasks or movements. In various embodiments, the invention further allows for the desired motion cancellation of the one or more joints in a non-moving subset (or locked set) of joints while still allowing movement of the locked set of joints for various other movements, such as movements based on autonomous algorithms or a commanded reconfiguration movement.

In certain aspects, a commanded end effector movement within a surgical space is effected by driving one or more joints of the manipulator according to a coordinated end effector displacing movement of the joints calculated by a processor using the kinematic Jacobian that is augmented to perform various other tasks, such as a reconfiguration movement or an auxiliary task such as a collision avoidance movement. Such tasks may be effected while maintaining the desired state of the end effector, often concurrent with the end effector displacing movement, according to coordinated movements of the joints calculated using such an augmented Jacobian.

In some embodiments, calculated movement relating to various other tasks, such as an avoidance movement based on an autonomous algorithm, may overlay the cancellation movement so that he "locked joints" can still be moved to effect the various other tasks. Examples of such avoidance movement are described in U.S. Provisional Application No. 61/654,755 filed Jun. 1, 2012, entitled "Manipulator Arm-to-Patient Collision Avoidance Using a Null-Space;" and U.S. Provisional Application No. 61/654,773 filed Jun. 1, 2012, entitled "System and Methods for Avoiding Collisions Between Manipulator Arms Using a Null-Space," the disclosures of which are incorporated herein by reference in their entireties. The calculated movement that overlays the cancelled movement of the "locked out" joints, however, is not limited to the autonomous movement and may include various other movements, such as a commanded reconfiguration movement or various auxiliary movements.

Embodiments of the invention may include a user input which is configured to take advantage of the degrees of freedom of a manipulator structure. Rather than manually reconfiguring the manipulator, the input facilitates use of driven joints of the kinematic linkage to reconfigure the manipulator structure in response to entry of a reconfiguration command by a user. In various embodiments, the user input for receiving the reconfiguration command is incorporated into and/or disposed near the manipulator arm. In other embodiments, the input comprises a centralized input device to facilitate reconfiguration of one or more joints, such as a cluster of buttons on the patient side cart or a joystick. The input device for receiving the reconfiguration command may be separate from the input for receiving a manipulation command to effect movement of the end effector. A controller of the surgical system may include a processor with readable memory having joint controller programming instructions or code recorded thereon which allows the processor to derive suitable joint commands for driving the joints recorded thereon so as to allow the controller to effect the desired reconfiguration in response to entry of the reconfiguration command. It is appreciated, however, that the invention may be used in a manipulator arms with or without a reconfiguration feature.

In another aspect, due the redundant nature of the highly configurable manipulators, the commanded motion of the plurality of joints to achieve a desired movement of a distal end effector and/or the remote center may produce joint velocities that are undesirable, excessive kinetic energy associated with one or more joints, or may produce motion that does not meet a desired motion preference. Examples of undesirable joint velocities may include an undesirable combination of joint states, excessive joint velocities for one or more joints, or disproportional joint states. The present invention provides a desired movement, such as a combination of joint states or other such movements described herein, for one or more joints during commanded end effector movement.

Embodiments of the invention include a processor that augments the kindematic Jacobian so as to provide an avoidance movement which facilitates use of driven joints of the kinematic linkage to configure the manipulator structure within a null-space to avoid arm-to-arm collisions. In some embodiments, in response to a determination that a distance between a first reference geometry and a second reference geometry is less than desired, the first reference geometry corresponding to one or more parts of a first manipulator arm and the second reference geometry corresponding to one or more part of a second adjacent manipulator arms, the Jacobian is augments so that subsequent movements calculated using the Jacobian increase the distance between first and second manipulators. In other embodiments, the system includes additional manipulator arms each having a corresponding reference geometry, such as a third manipulator arm having a third reference geometry and a further manipulator having a fourth reference geometry. In such embodiments, the system may further determine a relative state between each of the reference geometries and an avoidance vector extending therebetween, such as, between each nearest points on one or more pairs of reference geometries or line segments, and calculate the avoidance movement of one or more of the manipulator arms for use in an augmentation of the Jacobian so that a sufficient distance between each manipulators can be maintained.

In certain embodiments, the system uses a defined reference geometry which corresponds to a portion of the manipulator having a range of motion that overlaps with an adjacent manipulator such that the portion is susceptible to a collision with the adjacent manipulators when each moves into the region of overlap within its respective range of motion. The first reference geometry may be a single point, or more typically multiple line segments that corresponds to linkages and/or protruding portions of the manipulator arm. The system then determines a relative state between the defined reference geometries of adjacent arms, of which the state may be any of a position, velocity or acceleration of the reference geometry. The relative state may be a distance between or may include a difference between the velocity vectors of each reference geometry.

In one aspect, a commanded end effector movement within a surgical space is effected by driving one or more joints of the manipulator according to a coordinated end effector displacing movement of the joints calculated by a processor using the kinematic Jacobian. Various other tasks, such as a reconfiguration movement or a collision avoidance movement, may be effected while maintaining the desired state of the end effector by driving one or more joints of the manipulator according to coordinated movement of the joints extending in a null-space that are calculated by using an augmentation of the Jacobian. In some aspects, these various other tasks may utilize unweighted joint velocities, such that the system can be configured to calculate both weighted and unweighted joint velocities within the same iteration or kernel. Such embodiments may utilize alternative methods to weight the joint velocities using the unweighted joint velocities so as to reduce the required calculations to determine the weighted joint velocities.

In some embodiments, calculated movement relating to various other tasks, such as an avoidance movement based on an autonomous algorithm, may overlay the calculated joint velocities to effect the various other tasks. Examples of such collision avoidance movements are described in U.S. Provisional Application No. 61/654,755 filed Jun. 1, 2012, entitled "Manipulator Arm-to-Patient Collision Avoidance Using a Null-Space;" and U.S. Provisional Application No. 61/654,773 filed Jun. 1, 2012, entitled "System and Methods for Avoiding Collisions Between Manipulator Arms Using a Null-Space," the disclosures of which are incorporated herein by reference in their entireties. Examples of such commanded reconfiguration are described in U.S. Provisional Application No. 61/654,764 filed Jun. 1, 2012, entitled "Commanded Reconfiguration of a Surgical Manipulator Using the Null-Space," the disclosure of which is incorporated herein by reference in its entirety.

In the following description, various embodiments of the present invention will be described. For purposes of explanation, specific configurations and details are set forth in order to provide a thorough understanding of the embodiments. However, it will also be apparent to one skilled in the art that the present invention may be practiced without various specific details. Furthermore, well-known features may be omitted or simplified in order not to obscure the embodiment being described.

Referring now to the drawings, in which like reference numerals represent like parts throughout the several views, FIG. 1A is an overhead view illustration of a Minimally Invasive Robotic Surgical (MIRS) system 10, in accordance with many embodiments, for use in performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 so as to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 1B:
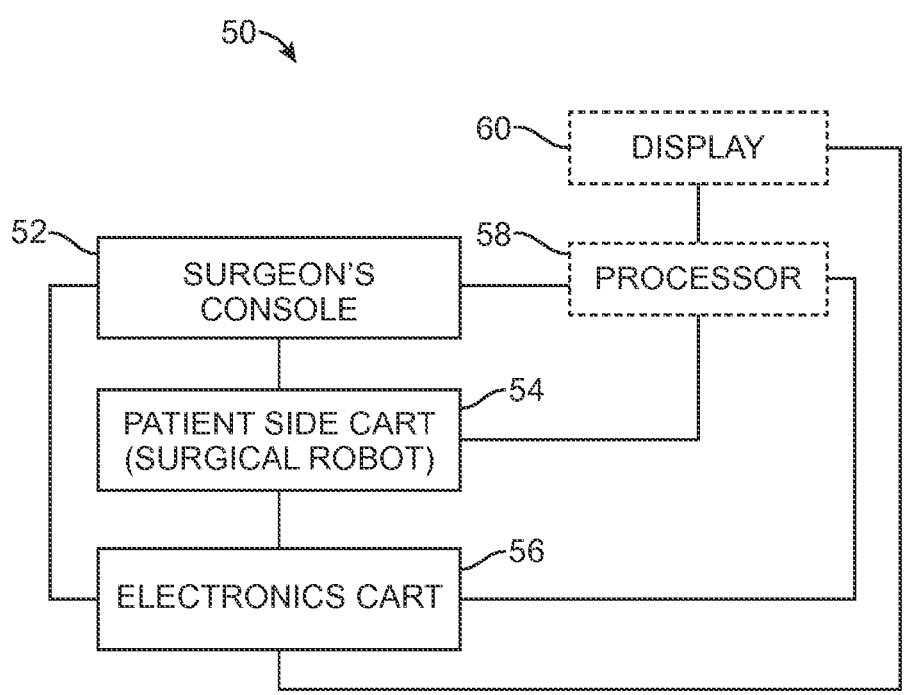
FIG. 1B diagrammatically illustrates the robotic surgical system of FIG. 1A.

FIG. 1B diagrammatically illustrates a robotic surgery system 50 (such as MIRS system 10 of FIG. 1A). As discussed above, a Surgeon's Console 52 (such as Surgeon's Console 16 in FIG. 1A) can be used by a Surgeon to control a Patient Side Cart (Surgical Robot) 54 (such as Patent Side Cart 22 in FIG. 1A) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1A). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, and can be used to process the captured images. The images can also be processed by a combination the Electronics Cart 56 and the processor 58, and can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 2:
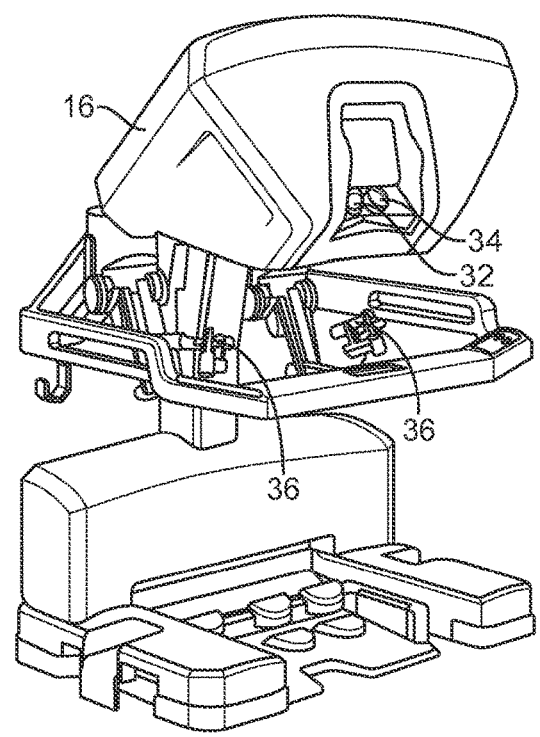
FIG. 2 is a perspective view illustrating a master surgeon console or workstation for inputting surgical procedure commands in the surgical system of FIG. 1A, the console including a processor for generating manipulator command signals in response to the input commands.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn causes the Patient Side Cart 22 (shown in FIG. 1A) to manipulate one or more tools. The input control devices 36 can provide the same degrees of freedom as their associated tools 26 (shown in FIG. 1A) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
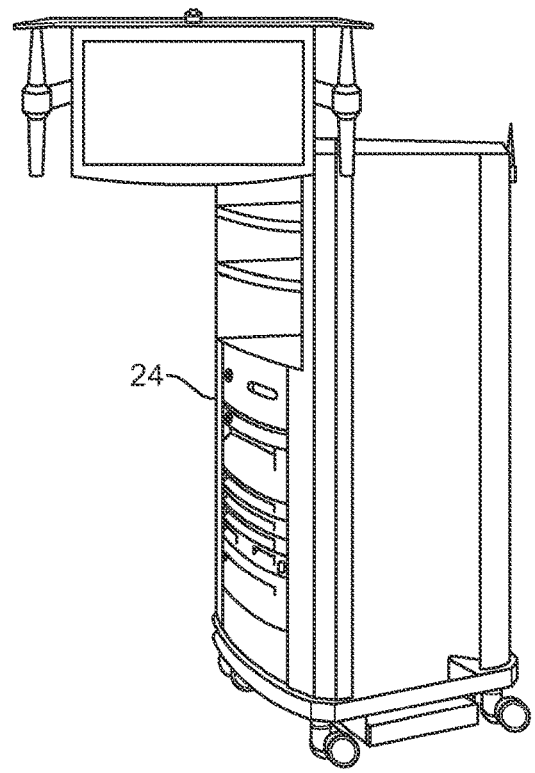
FIG. 3 is a perspective view of the electronics cart of FIG. 1A.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

Figure 4:
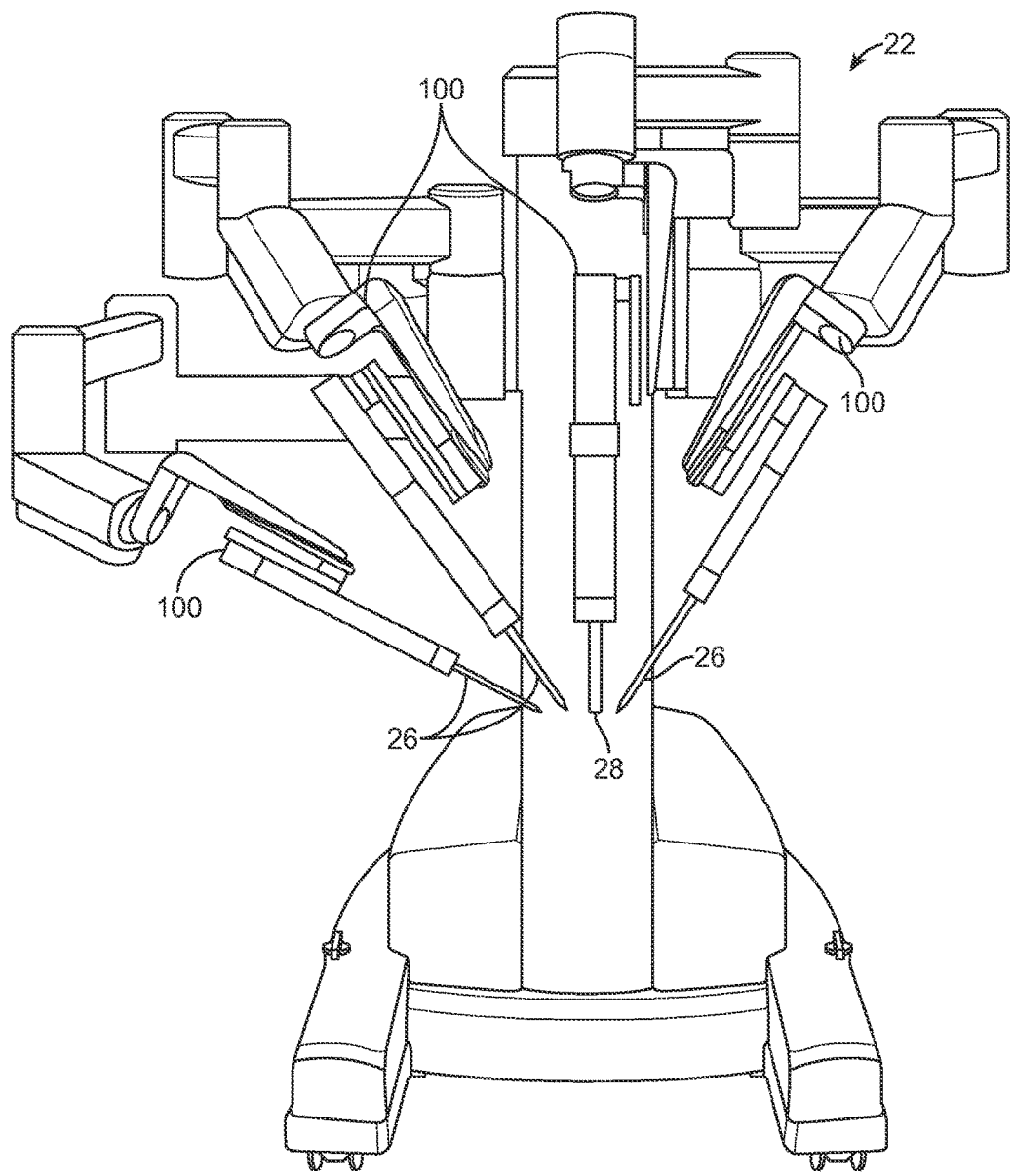
FIG. 4 is a perspective view of a patient side cart having four manipulator arms.

FIG. 4 shows a Patient Side Cart 22 having a plurality of manipulator arms, each supporting a surgical instrument or tool 26 at a distal end of the manipulator arm. The Patient Side Cart 22 shown includes four manipulator arms 100 which can be used to support either a surgical tool 26 or an imaging device 28, such as a stereoscopic endoscope used for the capture of images of the site of the procedure. Manipulation is provided by the robotic manipulator arms 100 having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical instruments or tools 26 when they are positioned within the field-of-view of the imaging device 28.

Regarding surgical tool 26, a variety of alternative robotic surgical tools or instruments of different types and differing end effectors may be used, with the instruments of at least some of the manipulators being removed and replaced during a surgical procedure. Several of these end effectors, including DeBakey Forceps, microforceps, Potts scissors, and clip applier include first and second end effector elements which pivot relative to each other so as to define a pair of end effector jaws. Other end effectors, including scalpel and electrocautery probe have a single end effector element. For instruments having end effector jaws, the jaws will often be actuated by squeezing the grip members of handle. Single end effector instruments may also be actuated by gripping of the grip members, for example, so as to energize an electrocautery probe.

The elongate shaft of instrument 26 allow the end effectors and the distal end of the shaft to be inserted distally into a surgical worksite through a minimally invasive aperture, often through an abdominal wall or the like. The surgical worksite may be insufflated, and movement of the end effectors within the patient will often be effected, at least in part, by pivoting of the instrument 26 about the location at which the shaft passes through the minimally invasive aperture. In other words, manipulators 100 will move the proximal housing of the instrument outside the patient so that shaft extends through a minimally invasive aperture location so as to help provide a desired movement of end effector. Hence, manipulators 100 will often undergo significant movement outside patient P during a surgical procedure.

Exemplary manipulator arms in accordance with many embodiments of the present invention can be understood with reference to FIGS. 5A-12C. As described above, a manipulator arm generally supports a distal instrument or surgical tool and effects movements of the instrument relative to a base. As a number of different instruments having differing end effectors may be sequentially mounted on each manipulator during a surgical procedure (typically with the help of a surgical assistant), a distal instrument holder will preferably allow rapid removal and replacement of the mounted instrument or tool. As can be understood with reference to FIG. 4, manipulators are proximally mounted to a base of the patient side cart. Typically, the manipulator arm includes a plurality of linkages and associated joints extending between the base and the distal instrument holder. In one aspect, an exemplary manipulator includes a plurality of joints having redundant degrees of freedom such that the joints of the manipulator arm can be driven into a range of differing configurations for a given end effector position. This may be the case for any of the embodiments of manipulator arms disclosed herein.

Figure 5A:
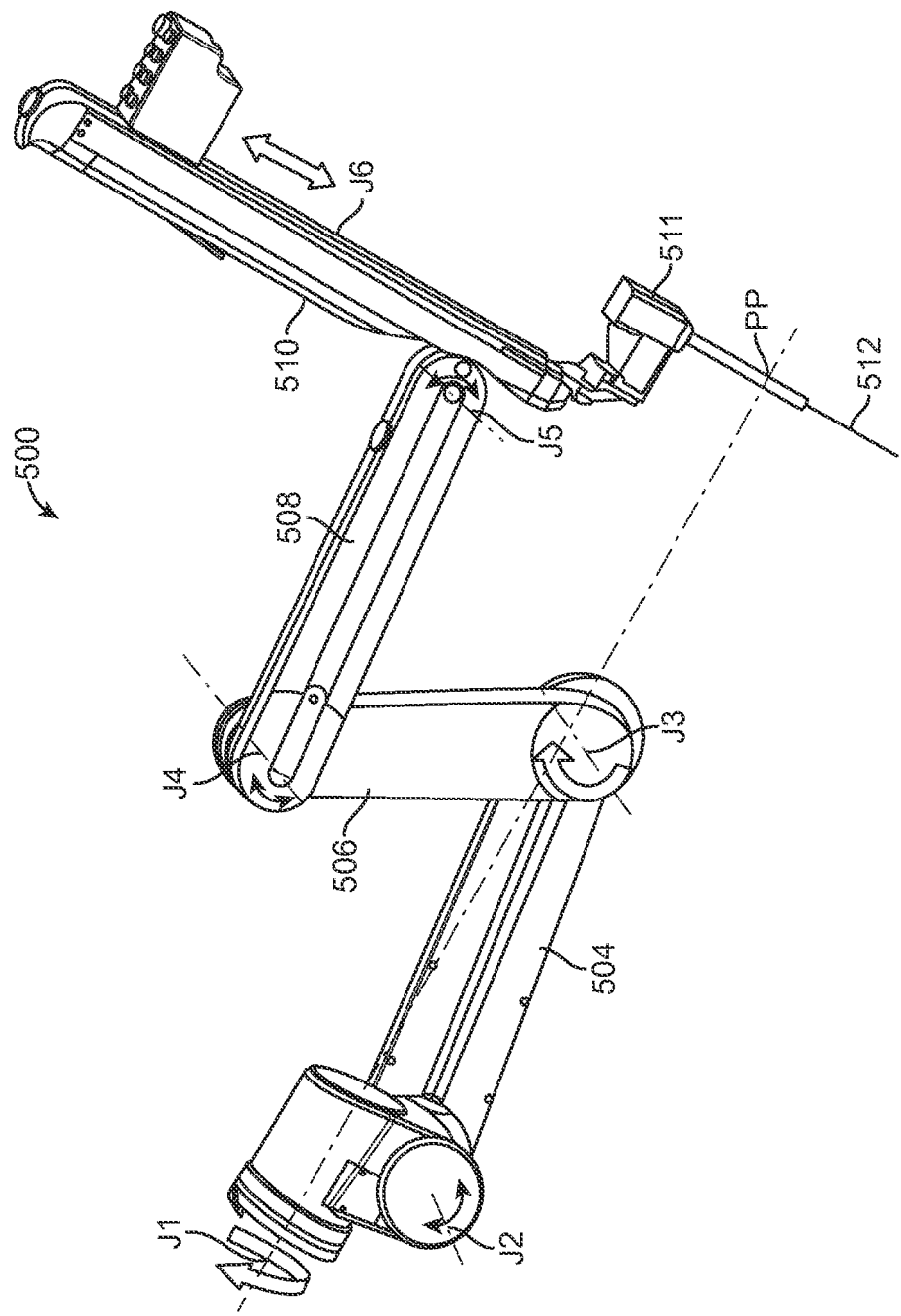
FIGS. 5A-5D show an example manipulator arm.

In many embodiments, such as shown for example in FIG. 5A, an exemplary manipulator arm includes a proximal revolute joint J1 that rotates about a first joint axis so as to revolve the manipulator arm distal of the joint about the joint axis. In some embodiments, revolute joint J1 is mounted directly to the base, while in other embodiments, joint J1 may be mounted to one or more movable linkages or joints. The joints of the manipulator, in combination, have redundant degrees of freedom such that the joints of the manipulator arm can be driven into a range of differing configurations for a given end effector position. For example, the manipulator arm of FIGS. 5A-5D may be maneuvered into differing configurations while the distal member 511 supported within the instrument holder 510 maintains a particular state and may include a given position or velocity of the end effector. Distal member 511 is typically a cannula through which the tool shaft 512 extends, and the instrument holder 510 is typically a carriage (shown as a brick-like structure that translates on a spar) to which the instrument attaches before extending through the cannula 511 into the body of the patient through the minimally invasive aperture.

Figure 5B:
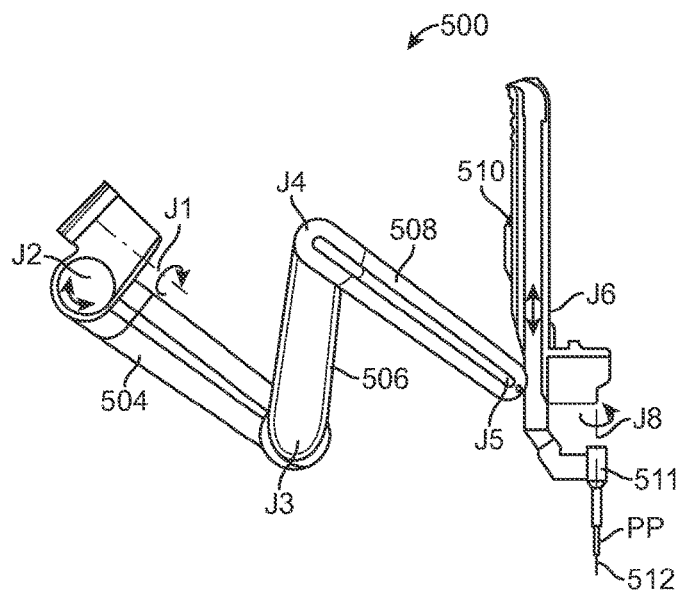
Figure 5D:
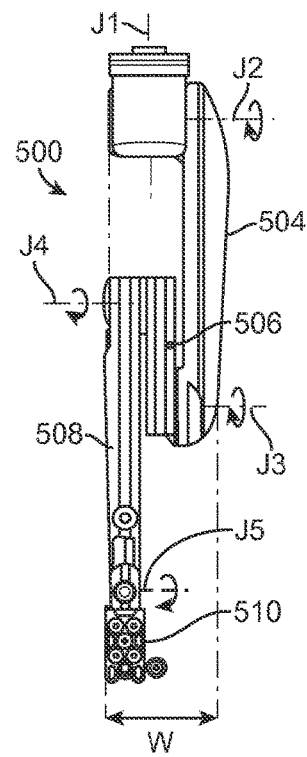
Figure 5C:
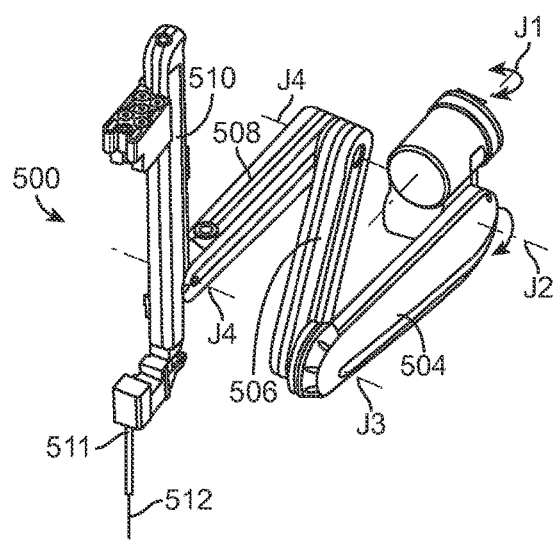

Describing the individual links of manipulator arm 500 of FIGS. 5A-5D along with the axes of rotation of the joints connecting the links as illustrated in FIG. 5A-5D, a first link 504 extends distally from a pivotal joint J2 which pivots about its joint axis and is coupled to revolute joint J1 which rotates about its joint axis. Many of the remainder of the joints can be identified by their associated rotational axes, as shown in FIG. 5A. For example, a distal end of first link 504 is coupled to a proximal end of a second link 506 at a pivotal joint J3 that pivots about its pivotal axis, and a proximal end of a third link 508 is coupled to the distal end of the second link 506 at a pivotal joint J4 that pivots about its axis, as shown. The distal end of the third link 508 is coupled to instrument holder 510 at pivotal joint J5. Typically, the pivotal axes of each of joints J2, J3, J4, and J5 are substantially parallel and the linkages appear "stacked" when positioned next to one another, as shown in FIG. 5D, so as to provide a reduced width w of the manipulator arm and improve patient clearance during maneuvering of the manipulator assembly. In many embodiments, the instrument holder also includes additional joints, such as a prismatic joint J6 that facilitates axial movement of instrument 306 through the minimally invasive aperture and facilitates attachment of the instrument holder to a cannula through which the instrument is slidably inserted.

The distal member or cannula 511 through which the tool 512 extends may include additional degrees of freedom distal of instrument holder 510. Actuation of the degrees of freedom of the instrument will often be driven by motors of the manipulator, and alternative embodiments may separate the instrument from the supporting manipulator structure at a quickly detachable instrument holder/instrument interface so that one or more joints shown here as being on the instrument are instead on the interface, or vice versa. In some embodiments, cannula 511 includes a rotational joint J7 (not shown) near or proximal of the insertion point of the tool tip or the pivot point PP, which generally is disposed at the site of a minimally invasive aperture. A distal wrist of the instrument allows pivotal motion of an end effector of surgical tool 512 about instrument joints axes of one or more joints at the instrument wrist. An angle between end effector jaw elements may be controlled independently of the end effector location and orientation.

The range of motion of an exemplary manipulator assembly can be appreciated by referring to FIGS. 6A-6C. During a surgical procedure, an exemplary manipulator arm can be maneuvered into a pitch forward configuration, as shown in FIG. 6A, or into a pitch back configuration, as shown in FIG. 6B, as needed to access particular patient tissues within a surgical workspace. A typical manipulator assembly includes an end effector that can pitch forwards and backwards about an axis by at least ±60 degrees, preferably by about ±75 degrees, and can also yaw about an axis by ±80 degrees. Although this aspect allows for increased maneuverability of the end effector with the assembly, there may be configurations in which movement of the end effector may be limited, particularly when the manipulator arm is in the full pitch forward or full pitch back configuration as in FIGS. 6A and 6B. In one embodiment, the manipulator arm has a Range of Motion (ROM) of (+/−75 deg) for the outer pitch, and (+/−300 degrees) for the outer yaw joints, respectively. In some embodiments, the ROM may be increased for the outer pitch to provide a ROM larger than (+/−90 deg) in which case a cone of space in which joint movement is limited or impossible could be made to disappear entirely, although generally the inner sphere associated with insertion limitations would remain. It is appreciated that various embodiments may be configured to have increased or decreased ROM, that the above noted ROMs are provided for illustrative purposes, and further that the invention is not limited to the ROMs described herein.

FIG. 6C graphically represents the overall range of motion and workspace of the tool tip of the exemplary manipulator of FIGS. 5A-5B. Although the workspace is shown as hemisphere, it may also be represented as a sphere depending on the range of motion and configuration of one or more revolute joints of the manipulator, such as joint J1. As shown, the hemisphere in FIG. 6C includes a central, small spherical void as well as two conical voids. The voids represent the areas in which movement of the tool tip may be impossible due to mechanical constraints or unfeasible due to extremely high joint velocities that make movement of the end effector difficult or slow. For these reasons, the conical void are referred to as the "cone of silence." In some embodiments, the manipulator arm may reach a singularity at a point within the cone. Since movement of the manipulator within or near the cone of silence may be impaired, it can be difficult to move the manipulator arm away from the cone of silence without manually moving one or more links of the manipulator to reconfigure the linkages and joints of the manipulator, which may require an alternative operating mode and delays the surgical procedure.

Movement of the instrument shaft into or near these conical portions typically occurs when the angle between distal linkages in the manipulator is relatively small. Thus, such configurations can be avoided by anisotropically emphasizing movement of the manipulator so as to increase the angles between linkages (so that the linkages are moved into a more orthogonal position relative to each other). For example, in the configurations shown in FIGS. 6A and 6B, when the angle between the distal most link and the instrument holder (angle a) becomes relatively small movement of the manipulator may become more difficult. Depending on the range of joint movements in the remaining joints in various embodiments, when the angle between certain linkages decreases, movement of the manipulator may be inhibited and in some cases, the manipulator arm may no longer be redundant. A manipulator configuration in which the instrument shaft nears these conical portions, or in which the angles between linkages are relatively low is said to be "poorly conditioned" such that maneuverability and dexterity of the manipulator arm is limited. It is desirable that the manipulator be "well conditioned" so as to maintain dexterity and range of movement. In one aspect, the present invention allows a user to avoid movement of the instrument shaft near the above described conical portions by simply entering a command to reconfigure the manipulator as desired, even during movement of the end effector in a surgical procedure. This aspect is particularly useful should the manipulator, for whatever reason, become "poorly conditioned."

While the embodiments of the manipulator described above may be utilized in the present invention, some embodiments may include additional joints, which may also be used to improve dexterity and the conditioning of the manipulator arm. For example, an exemplary manipulator may include a revolute joint and/or linkage proximal of joint J1 which can be used to revolve the manipulator arm of FIG. 5A, and its associated cone of silence, about an axis of the revolute joint so as to reduce or eliminate the cone of silence. In another embodiment, the exemplary manipulator may also include a distal pivotal joint that pivots the instrument holder about an axis substantially perpendicular to joint J5, thereby offsetting the tool tip so as to further reduce the cone of silence and improve the range of movement of the surgical tool. In still another embodiment, a proximal joint of the manipulator arm, such as J1, may be movably mounted on the base, so as to move or shift the cone of silence as needed and improve the range of motion of the manipulator tool tip. The use and advantages of such additional joints can be understood by referring to FIGS. 7A-12C, which illustrate examples of such joints, which may each be used independent of one another or used in combination, in any of the exemplary manipulator arms described herein.

Figure 7A:
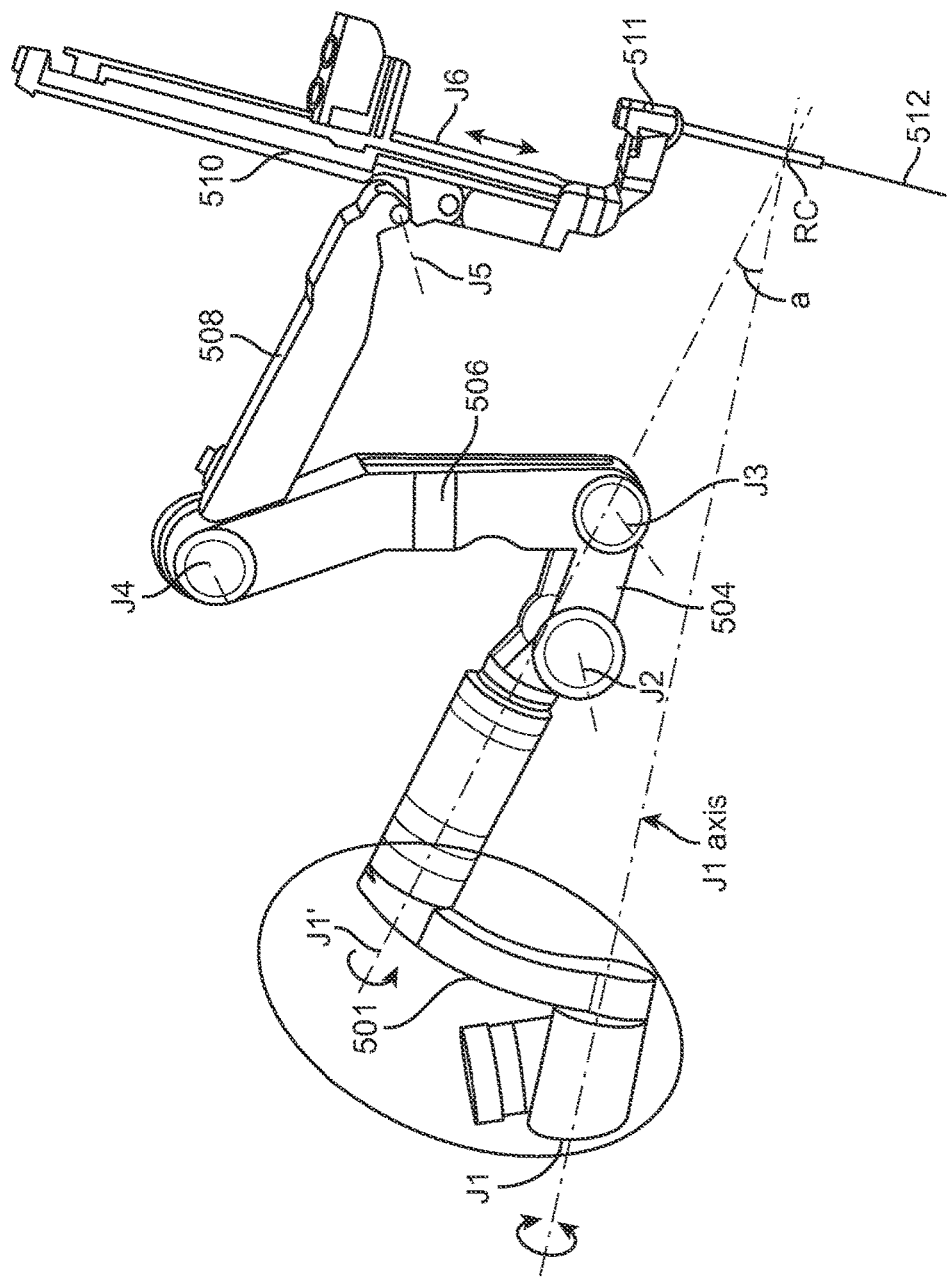
FIG. 7A shows example manipulator arms having a proximal revolute joint that revolves the manipulator arm about an axis of a proximal revolute joint.
Figure 7B:
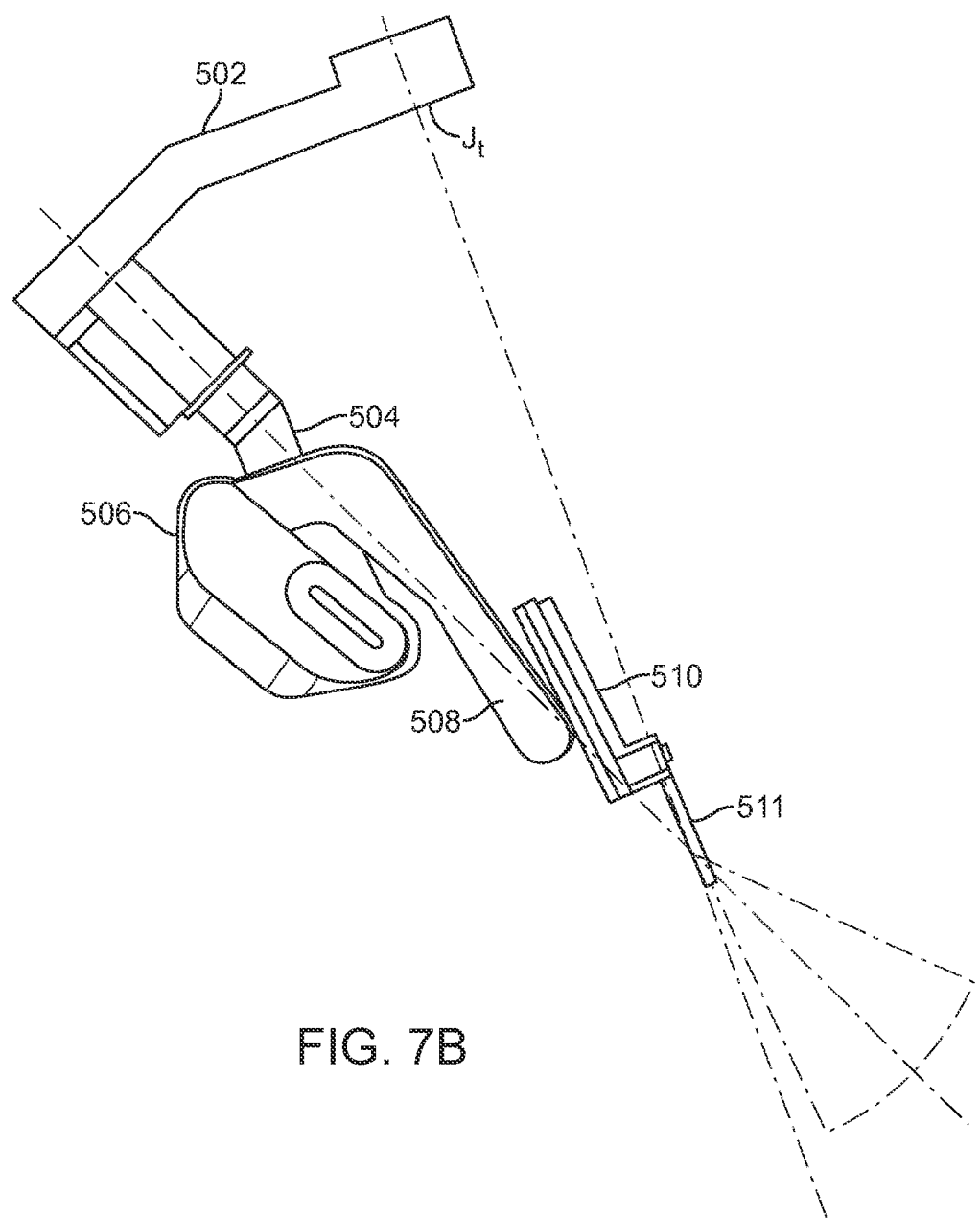
FIG. 7B shows an example manipulator arm and the associated range of motion and cone of silence, the exemplary manipulator arm having a proximal revolute joint that revolves the manipulator arm around an axis of a proximal revolute joint the movement of which can be used to mitigate the depicted cone of silence.

FIGS. 7A-7B illustrate an additional redundant joint for use with exemplary manipulator arms—a first joint coupling a proximal portion of the manipulator arm to the base. The first joint is a proximal revolute joint J1 that revolves the manipulator arm about a joint axis of joint J1. The proximal revolute J1 includes a link 501 that offsets joint J1' from the proximal revolute J1 by a pre-determined distance or angle. The link 501 can be a curved linkage, as shown in FIG. 7A, or a linear or angled linkage, as shown in FIG. 7B. Typically, the joint axis of the joint J1 is aligned with the remote center RC or insertion point of the tool tip, as shown in each of FIG. 7A. In an exemplary embodiment, the joint axis of joint J1 passes through the remote center, as does each other revolute joint axis in the manipulator arm, to prevent motion at the body wall and can therefore be moved during surgery. The axis of joint J1 is coupled to a proximal portion of the arm so it can be used to change the position and orientation of the back of the arm. In general, redundant axes, such as this, allow the instrument tip to follow the surgeon's commands while simultaneously avoiding collisions with other arms or patient anatomy. In one aspect, the proximal revolute J1 is used solely to change the mounting angle of the manipulator with respect to the floor. This angle is important in order to 1) avoid collisions with external patient anatomy and 2) reach anatomy inside the body. Typically, the angle a between the proximal link of the manipulator attached to the proximal revolute joint J1 and the axis of the proximal revolute is about 15 degrees.

FIG. 7B illustrates the relationship of the proximal revolute joint J1 and its associated joint axis and the cone of silence in an exemplary manipulator arm. The joint axis of the proximal revolute joint J1 may pass through the cone of silence or may be completely outside of the cone of silence. By revolving the manipulator arm about the axis of the proximal revolute J1, the cone of silence can be reduced (in an embodiment where the joint J1 axis passes through the cone of silence), or can be effectively eliminated (in an embodiment where the proximal revolute joint axis extends completely outside the cone of silence). The distance and angle of the link 501 determines the position of the joint J1 axis relative to the cone of silence.

Figure 8:
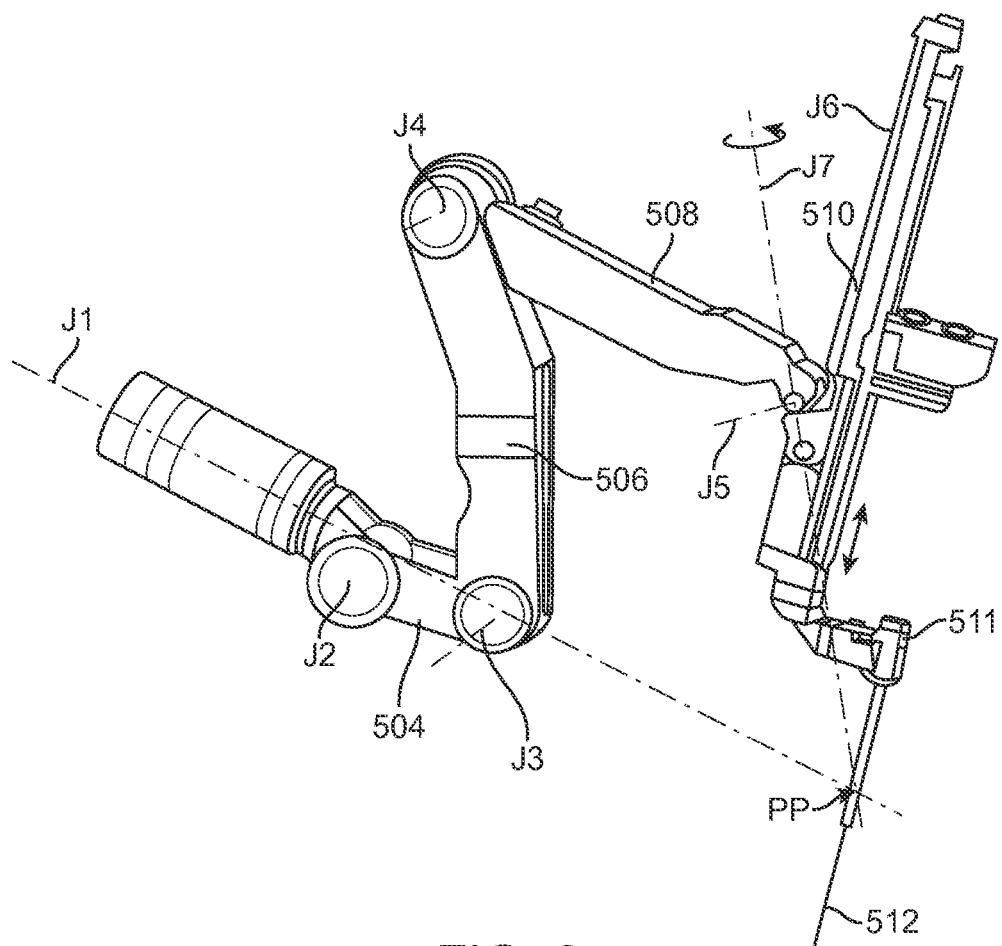
FIG. 8 shows an example manipulator arm having a revolute joint near the distal instrument holder.
Figure 9:
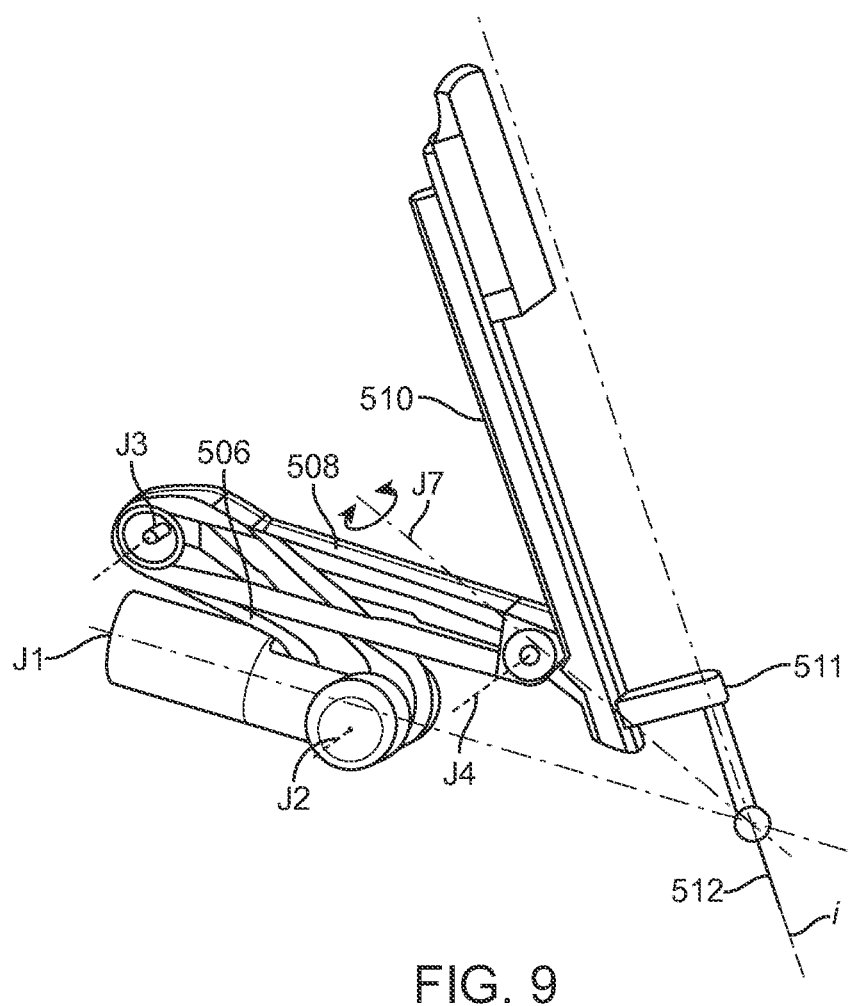
FIG. 9 shows an example manipulator arm having a revolute joint near the distal instrument holder that revolves or twists the instrument holder about the joint axis.
Figure 10A:
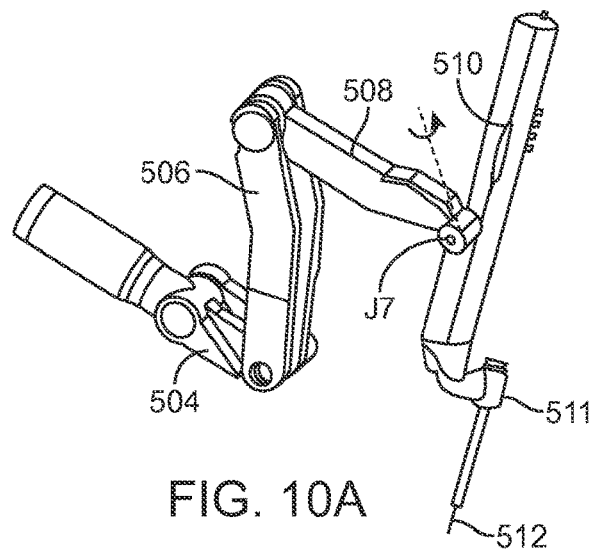
FIGS. 10A-10C show sequential views of an exemplary manipulator arm having a revolute joint near a distal instrument holder as the joint is moved throughout its range of joint movement.
Figure 10B:
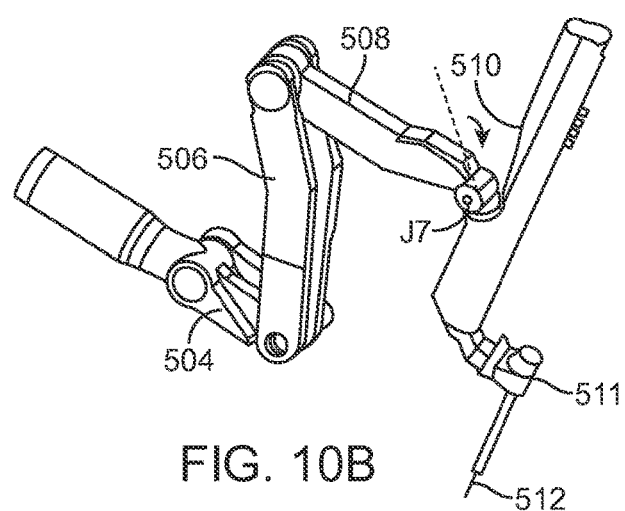
Figure 10C:
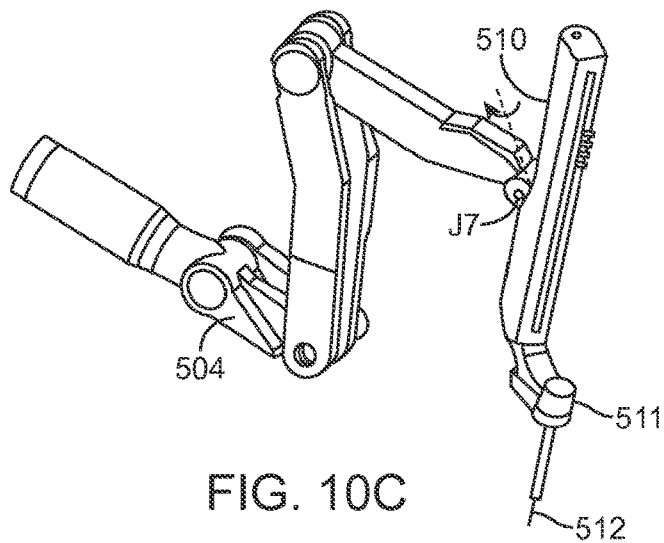

FIG. 8 illustrates another type of redundant joint for use with exemplary manipulator arms, a distal revolute joint J7 coupling the instrument holder 510 to a distal link of the manipulator arm 508. The distal revolute joint J7 allows the system to twist the instrument holder 510 about the joint axis, which typically passes through the remote center or insertion point. Ideally, the revolute joint is located distally on the arm and is therefore particularly well suited to moving the orientation of the insertion axis. The addition of this redundant axis allows the manipulator to assume multiple positions for any single instrument tip position. In general, redundant axes, such as this, allow the instrument tip to follow the surgeon's commands while simultaneously avoiding collisions with other arms or patient anatomy. Because the distal revolute joint J7 has the ability to move the insertion axis closer to the yaw axis, it is able to increase arm pitch back range of motion. The relationship between the axis of the distal revolute joint J7, the yaw axis of J1' and the insertion axis of tool tip is shown in FIG. 9. FIGS. 10A-10C show the sequential movement of the J7 and how it shifts the insertion axis of tool tip from side to side.

Figure 11A:
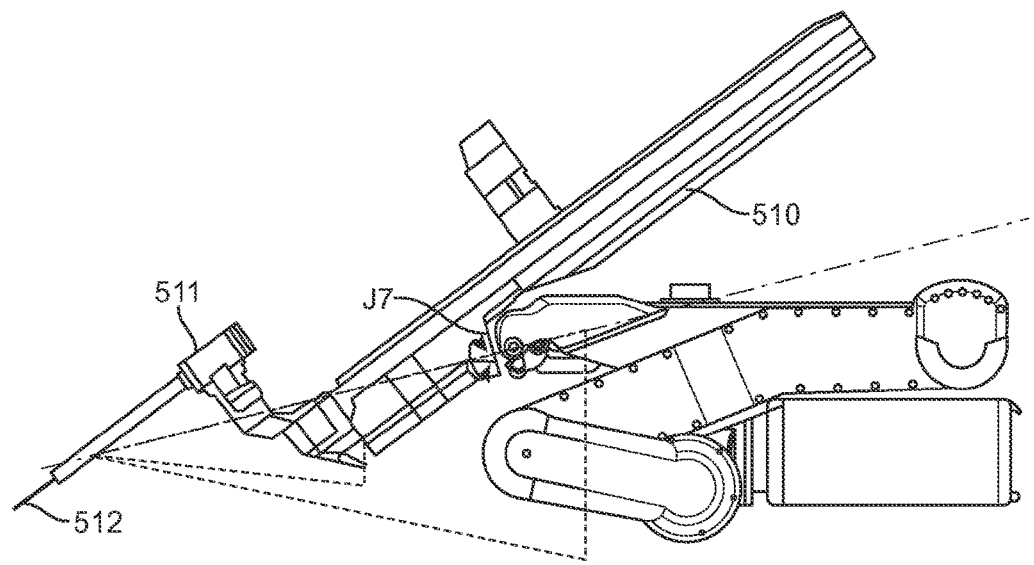
FIGS. 11A-11B show the revolved profile of an exemplary manipulator arm having a distal revolute joint when the angular displacement of the joint is 0° versus an angular displacement of 90°, respectively.
Figure 11B:
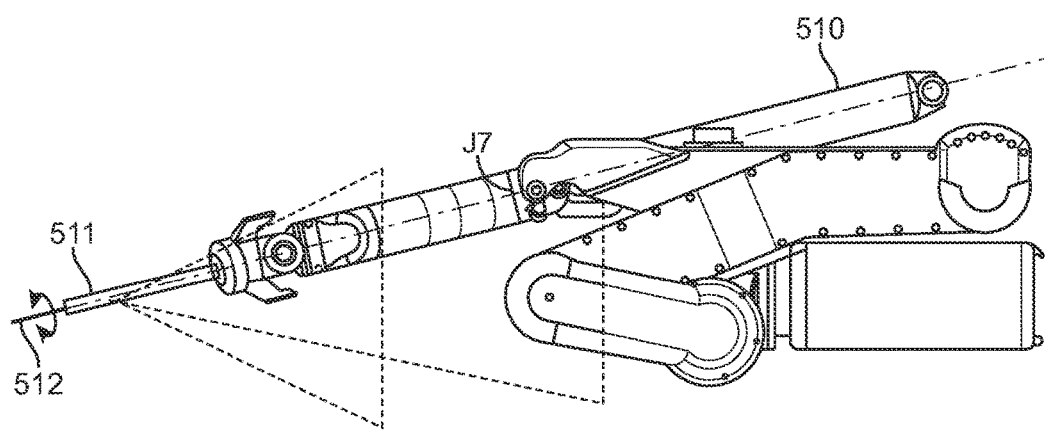

Another advantage of the distal revolute joint J7 is that it may reduce the patient clearance cone, which is the swept volume of the distal portion of the manipulator arm proximal of the insertion point which must clear the patient to avoid collision between the patient and the instrument holder or distal linkages of the manipulator arm. FIG. 11A illustrates the patient clearance cone of the proximal portion of the manipulator arm while the angular displacement of the distal revolute joint remains at 0°. FIG. 11B illustrates the reduced patient clearance cone of the proximal portion of the manipulator arm while the distal revolute joint is shown having an angular displacement of 90° about its axis. Thus, in procedures having minimal patient clearance near the insertion point, use of the joint J7 in accordance with the present invention may provide additional clearance while maintaining the remote center location or the position of the end effector as desired.

Figure 12A:
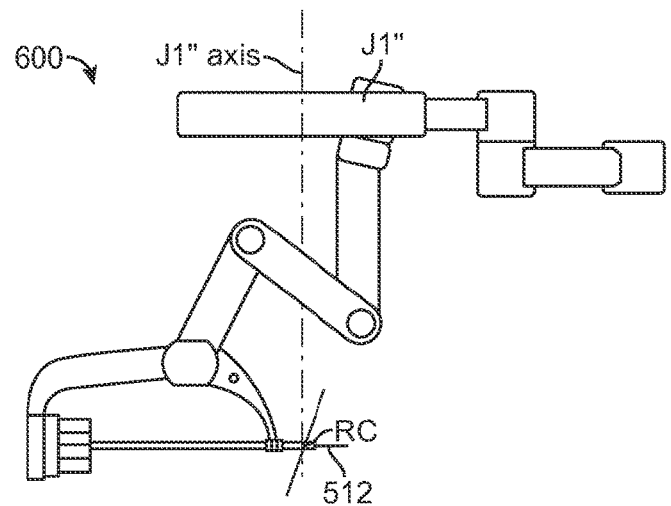
Figures 12B, 12C:
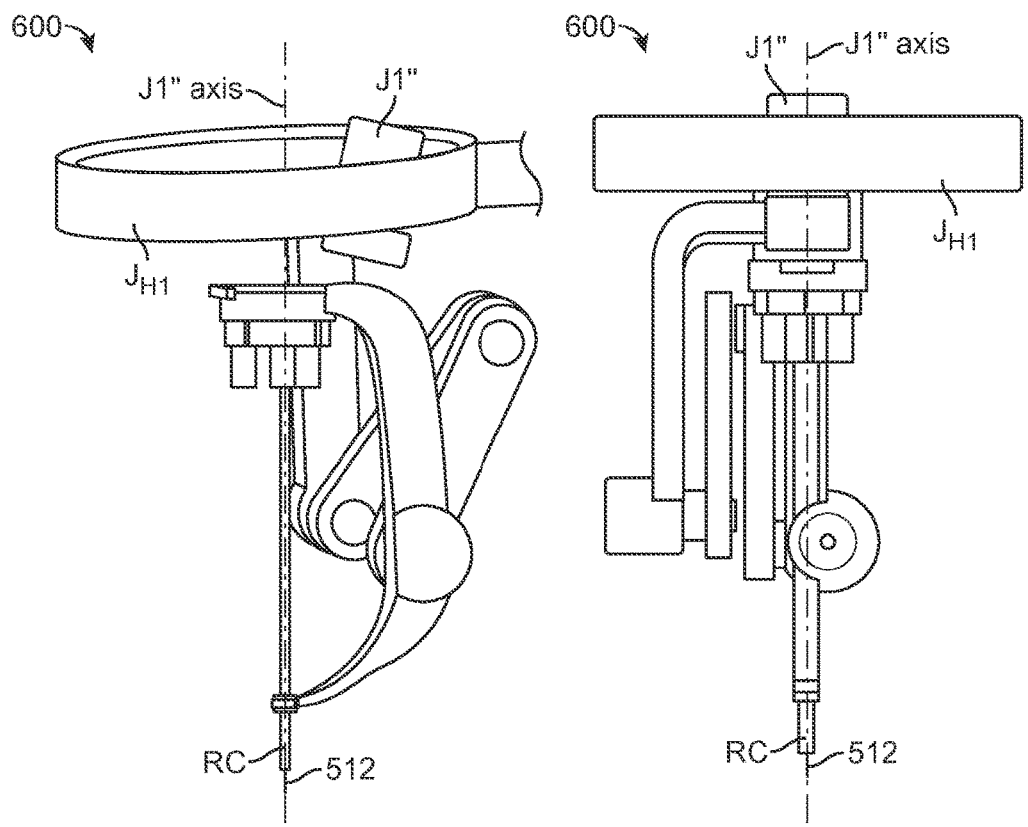

FIGS. 12A-12C illustrate another type of redundant joint for use with exemplary manipulator arms, a proximal joint that translates or revolves the manipulator arm about an axis. In many embodiments, this proximal translatable joint translates a proximal joint of the manipulator, such as joint J1 or J1', along a path so as to reduce or eliminate the cone of silence by shifting or rotating the range of motion of the manipulator arm to provide for better conditioning and improved maneuverability of the manipulator arm. The translatable joint may include a circular path, such as shown in joint J1" in FIGS. 12A-12D, or may include a semicircular or arcuate path. Generally, the joint revolves the manipulator arm about an axis of the translatable joint that intersects with the remote center RC about which the shaft of the tool 512 extending through cannula 511 pivots. In the embodiments shown this axis of J1" is a vertical axis, although in various other embodiments the axis may be at an angle or horizontal.

In some embodiments, the manipulator arm 500 may include any or all of the proximal and distal revolute joint, a proximal translatable joint and a parallelogram configuration of the distal linkages. Use of any or all of these features provide additional redundant degrees of freedom and facilitate reconfiguration in accordance with the present invention so as to provide for a better "conditioned" manipulator assembly by increasing the angles between linkages thereby improving the dexterity and motion of the manipulator. The increased flexibility of this exemplary manipulator can also be used to optimize the kinematics of the manipulator linkage so as to avoid joint limits, singularities, and the like.

In an example embodiment, the joint movements of the manipulator are controlled by driving one or more joints by a controller using motors of the system, the joints being driven according to coordinated and joint movements calculated by a processor of the controller. Mathematically, the controller may perform at least some of the calculations of the joint commands using vectors and/or matrices, some of which may have elements corresponding to configurations or velocities of the joints. The range of alternative joint configurations available to the processor may be conceptualized as a joint space. The joint space may, for example, have as many dimensions as the manipulator has degrees of freedom, and a particular configuration of the manipulator may represent a particular point in the joint space, with each coordinate corresponding to a joint state of an associated joint of the manipulator.

In an example embodiment, the system includes a controller in which a commanded position and velocity of a feature in the work-space, denoted here as its Cartesian space, are inputs. The feature may be any feature on the manipulator or off the manipulator which can be used as a control frame to be articulated using control inputs. An example of a feature on the manipulator, used in many examples described herein, would be the tool-tip. Another example of a feature on the manipulator would be a physical feature which is not on the tool-tip, but is a part of the manipulator, such as a pin or a painted pattern. An example of a feature off the manipulator would be a reference point in empty space which is exactly a certain distance and angle away from the tool-tip. Another example of a feature off the manipulator would be a target tissue whose position relative to the manipulator can be established. In all these cases, the end effector is associated with an imaginary control frame which is to be articulated using control inputs. However, in the following, the "end effector" and the "tool tip" are used synonymously. Although generally, there is no closed form relationship which maps a desired Cartesian space end effector position to an equivalent joint-space position, there is generally a closed form relationship between the Cartesian space end effector and joint-space velocities. The kinematic Jacobian is the matrix of partial derivatives of Cartesian space position elements of the end effector with respect to joint space position elements. In this way, the kinematic Jacobian captures the kinematic relationship between the end effector and the joints. In other words, the kinematic Jacobian captures the effect of joint motion on the end effector. The kinematic Jacobian (J) can be used to map joint-space velocities (dq/dt) to Cartesian space end effector velocities (dx/dt) using the relationship below:

$$dx/dt = J\,dq/dt$$

Thus, even when there is no closed-form mapping between input and output positions, mappings of the velocities can iteratively be used, such as in a Jacobian-based controller to implement a movement of the manipulator from a commanded user input, however a variety of implementations can be used. Although many embodiments include a Jacobian-based controller, some implementations may use a variety of controllers that may be configured to access the Jacobian of the manipulator arm to provide any of the features described herein.

One such implementation is described in simplified terms below. The commanded joint position is used to calculate the Jacobian (J). During each time step ($\Delta t$) a Cartesian space velocity (dx/dt) is calculated to perform the desired move ($dx_{des}/dt$) and to correct for built up deviation ($\Delta x$) from the desired Cartesian space position. This Cartesian space velocity is then converted into a joint-space velocity (dq/dt) using the pseudo-inverse of the Jacobian ($J^{\#}$). The resulting joint-space commanded velocity is then integrated to produce joint-space commanded position (q). These relationships are listed below:

$$dx/dt = dx_{des}/dt + k\Delta x \qquad (1)$$

$$dq/dt = J^{\#}\,dx/dt \qquad (2)$$

$$q_i = q_{i-1} + dq/dt\,\Delta t \qquad (3)$$

The pseudo-inverse of the Jacobian (J) directly maps the desired tool tip motion (and, in some cases, a remote center of pivotal tool motion) into the joint velocity space. If the manipulator being used has more useful joint axes than tool tip degrees of freedom (up to six), (and when a remote center of tool motion is in use, the manipulator should have an additional 3 joint axes for the 3 degrees of freedom associated with location of the remote center), then the manipulator is said to be redundant. A redundant manipulator's Jacobian includes a "null-space" having a dimension of at least one. In this context, the "null-space" of the Jacobian (N(J)) is the space of joint velocities which instantaneously achieves no tool tip motion (and when a remote center is used, no movement of the pivotal point location); and "null-motion" is the combination, trajectory or path of joint positions which also produces no instantaneous movement of the tool tip and/or location of the remote center.

In one approach, the joint states are separated into "null-perpendicular" movements, that is joint states that achieve a commanded tool tip state and "null-space" joint movements, that is joint states that result in no tool tip motion (or when remote software center is used, no movement of the remote center or pivotal point location). Incorporating or injecting the calculated null-space velocities into the control system of the manipulator to achieve the desired reconfiguration of the manipulator (including any reconfigurations described herein) changes above equation (2) to the following:

$$dq/dt = dq_{perp}/dt + dq_{null}/dt \qquad (4)$$

$$dq_{perp}/dt = J^{\#}\,dx/dt \qquad (5)$$

$$dq_{null}/dt = (1 - J^{\#}J)z = V_n V_n^T z = V_n \alpha \qquad (6)$$

The joint velocity according to Equation (4) has two components: the first being the null-perpendicular-space component, the "purest" joint velocity (shortest vector length) which produces the desired tool tip motion (and when the remote center is used, the desired remote center motion) and the second being the null-space component. Equations (2) and (5) show that without a null-space component, the same equation is achieved. Equation (6) starts with a traditional form for the null-space component on the left, and on the far right side, shows the form used in an exemplary system, wherein $V_n$ is the set of orthonormal basis vectors for the null-space, and $\alpha$ are the coefficients for blending those basis vectors. In some embodiments, a is determined by control parameters, variables or setting, such as by use of knobs or other control means, to shape or control the motion within the null-space as desired. Although this approach has many benefits, in some calculated movements, the complexity and cycle time required to calculate the joint movements for each of the "null-perpendicular" and "null-space" joint states for use in a combined movements may be greater than desired.

In an alternative, an augmented Jacobian approach may be used that incorporates one or more auxiliary functions or desired movements associated with null-space movements within a function, coefficient or joint state used to augment the Jacobian. In one aspect, this approach incorporates a potential function gradient associated with the one or more auxiliary functions or desired movement, which is applied to the Cartesian Space end effector velocities may be used. The Jacobian may be augmented so that the resulting joint velocities calculated by taking a pseudo-inverse of the Jacobian provide the desired auxiliary task or movement. In accordance with the augmented Jacobian approach, the following equations may be used, although it is appreciated that column vectors may be used:

$$dx/dt = J * dq/dt$$

$$y = h(q, \ldots)$$

$$dy/dt = \partial h/\partial q * dq/dt$$

$$[dx/dt^T dy/dt^T]^T = [J^T \partial h/\partial q^T]^T * dq/dt$$

$$d[x^T y^T]^T/dt = [J^T \partial h/\partial q^T]^T * dq/dt$$

$$dq/dt = [J^T \partial h/\partial q^T]^{T\#} d[x^T y^T]^T/dt$$

This approach may provide simplified calculations hence reduced calculation times as compared to the previous approach above. In some commanded movements, this alternative approach may reduce the calculation time for joint velocities in providing the calculated joint velocities that achieve the commanded end effector or tool tip movement concurrent with the one or more auxiliary functions or desired movements of one or more other joints of the manipulator. In certain aspects, this approach may be used in combination with (e.g. alternating between or intermittently) with the above approach in order to retain the advantages associated with each approach as needed. For example, in some embodiments, the system may utilize an augmented Jacobian approach may be used for one or more auxiliary functions (e.g. collision avoidance, commanded reconfiguration) when one or more joints of the manipulator are not near their respective joint limits or a singularity and may utilize the first approach above when the one or more joints are at their respective limits or at a singularity. It is understood that in referring to calculating joint movements using the Jacobian, described herein, such calculations may include use of the augmented Jacobian approach.

In one aspect, the Jacobian may be augmented, as described above, to achieve one or more auxiliary functions or desired joint movements. In some embodiments, to achieve the one or more auxiliary functions or desired joint movements that may include performing a specific tasks or combination of joint movements or generally moving one or more joints in a desired direction or toward specific joint states or relative states in order to achieve the auxiliary task. The one or more auxiliary functions or desired joint movements for which an augmented Jacobian may include any of: commanded end effector movement, pivoting movements, controlled movement of the pivotal center according to a desired movement (e.g. port clutch, motion compensation); joint motion cancellation, collision avoidance between adjacent manipulator arms or between a manipulator and a patient, commanded reconfiguration of one or more joints of the manipulator, a pitch-null float feature, facilitated access to edges of Cartesian-coordinate space, emphasizing joint motion anisotropically or any combination thereof. In one aspect, any of these features can be combined within a function to obtain a coefficient with which the Jacobian can be augmented. These features can be weighted, scaled, or selectively filtered before and/or after application to the Jacobian so as to provide calculated joint movements that combine auxiliary tasks or desired joint movements as desired.

In one aspect, certain features may be performed as a primary task such that certain other features could be performed by the augmented Jacobin as an auxiliary task. For example, maintaining a desired pivotal center location (or providing controlled movement of a pivotal center at a remote software center) may be performed as a primary task in calculation of the Jacobian while the Jacobian may be augmented to perform the commanded end effector movement as an auxiliary task. It is appreciated that this same concept may be applied to various other combinations of tasks or movements performing one movement as a primary task while using the augmentation to perform another movement as an auxiliary task.

Figure 14A:
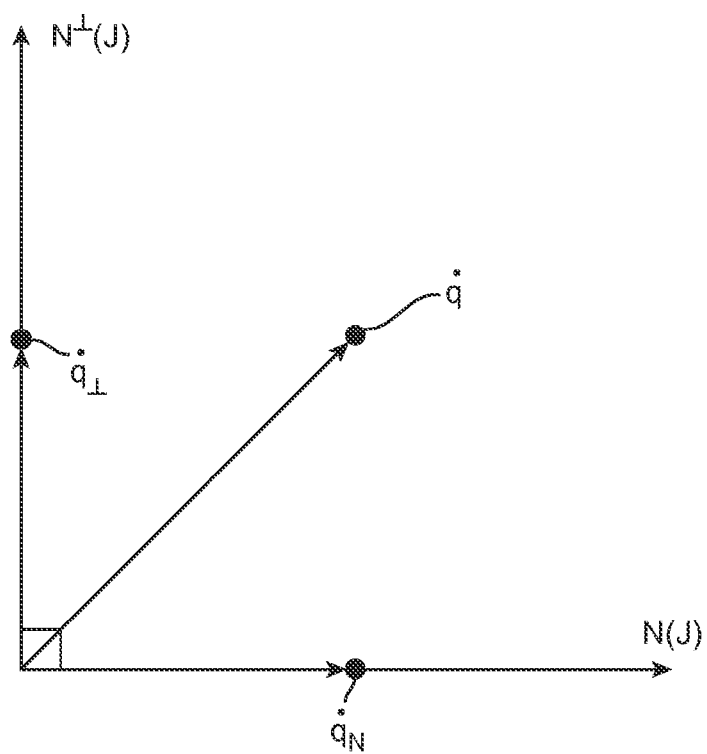
FIGS. 14A-14B graphically represent the relationship between the null-space and the null-perpendicular-space of the Jacobian of an example manipulator assembly.
Figure 14B:
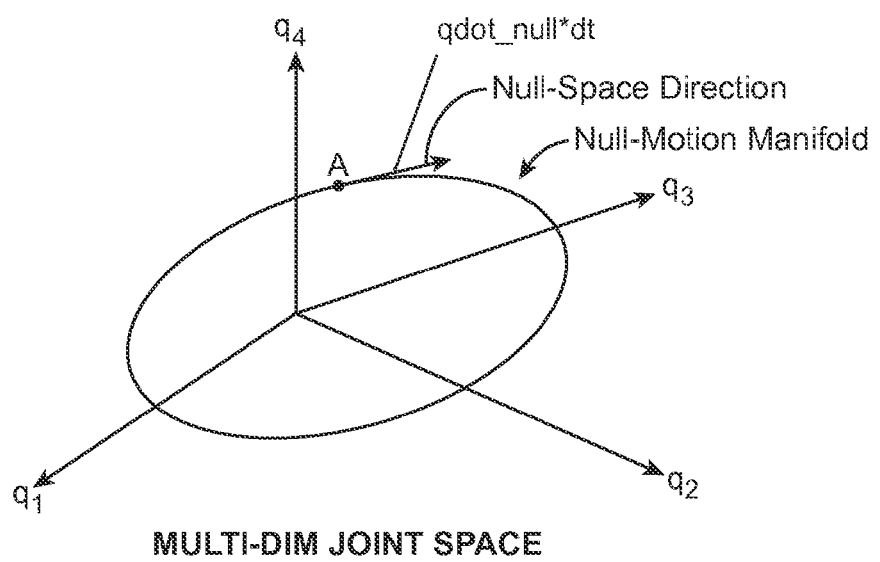

FIGS. 14A-14B graphically illustrate the relationship between the null-space of the Jacobian and the null-perpendicular-space of the Jacobian of an exemplary manipulator arm. FIG. 14A shows a two-dimensional schematic showing the null-space along the horizontal axis, and the null-perpendicular-space along the vertical axis, the two axes being orthogonal to one another. The diagonal vector represents the sum of a velocity vector in the null-space and a velocity vector in the null-perpendicular-space, which is representative of Equation (4) above or alternatively may be obtained by use of an augmented Jacobian as descried herein and as would be understood by one of skill in the art.

FIG. 14B graphically illustrates the relationship between the null-space and the null-motion manifold within a four-dimensional joint space, shown as the "null-motion manifold." Each arrow (q1, q2, q3, and q4) representing a principal joint axis. The closed curve represents a null-motion manifold which is a set of joint-space positions which instantaneously achieves the same end effector position. For a given point A on the curve, since the null-space is a space of joint velocities which instantaneously produce no movement of the end effector, the null-space is parallel to the tangent of the null-motion manifold at point A.

In one aspect, the Jacobian matrix, the pseudo-inverse of which is used to determine joint states to achieve a commanded tool tip state, can be augmented by a coefficient determined according to the desired auxiliary task or desired joint movement. When the auxiliary task desired include "locking" of one or more joints of the manipulator, the variable associated with movement of the joint desired to be locked can be forced to "0" by the augmentation to the Jacobian, for example, as shown in the following equations (although the term "J" is used in various figures to a joint, in the equations provided herein "J" denotes a Jacobian and q denotes a joint value):

$$\dot{x} = J\dot{q}$$

$$\begin{pmatrix} \dot{x} \\ y \end{pmatrix} = \begin{pmatrix} J \\ H \end{pmatrix}\dot{q}$$

$$\begin{pmatrix} \dot{x} \\ 0 \end{pmatrix} = \begin{pmatrix} J \\ \overline{001000 \ldots} \end{pmatrix}\dot{q}$$

$$\dot{x} = J\dot{q}$$

$$0 = \dot{q}_3$$

Figure 15A:
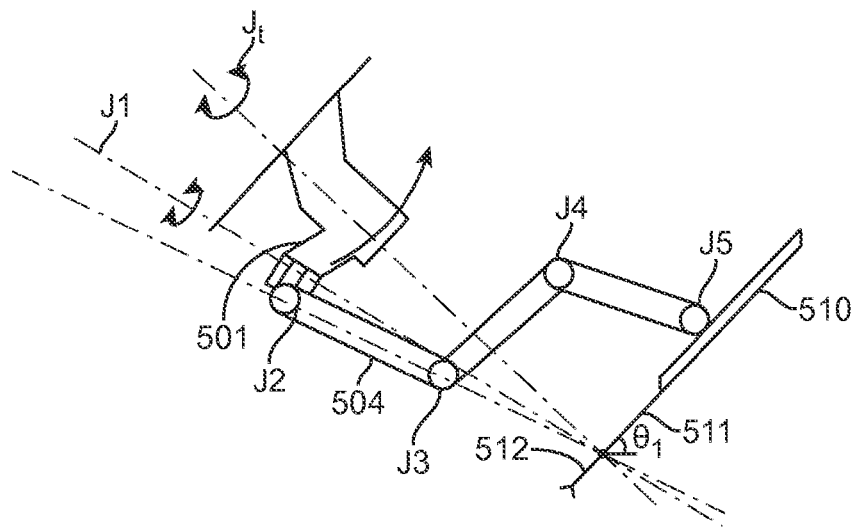
FIGS. 15A-15B illustrate movement of an example manipulator according to a reconfiguration movement concurrent with an end effector displacing movement in which the proximal-most joint is locked out of the end effector displacing movement.
Figure 15B:
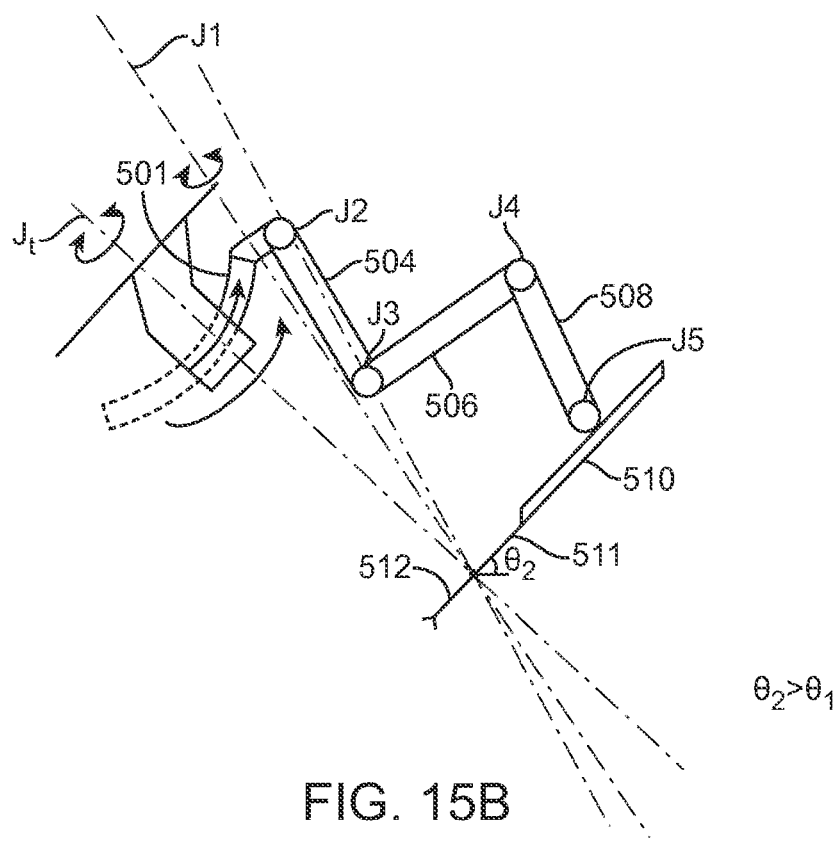

FIGS. 15A-15B schematically illustrate an example manipulator 500 before and after movement of a manipulator arm according to a commanded reconfiguration movement concurrent with an end effector displacing movement in which joint $J_t$ is locked out. In response to an end effector manipulation command entered by a user, the processor calculates movements of the joints, including joint $J_t$, by use of the kinematic Jacobian, which has been augmented to inhibit movement of one or more joints within a null-space, thereby effectively cancelling movement of locked joint $J_t$. This joint movement cancellation can be provided concurrent with the calculated joint movements that provide the desired effector movement, and further concurrent with a reconfiguration movement of one or more other joints in response to a user command to reconfigure the manipulator arm. As shown in the example of FIG. 15A-15B, the reconfiguration movement of the arm includes movement of joint $J_t$ such that even when joint $J_t$ is locked out of the end effector displacing movement, the locked joint can move when effecting movement relating to another task, such as commanded reconfiguration of the manipulator arm. In another aspect, this approach may be used so as to effectively lock out a desired joint of the plurality from any movement, that is the Jacobian is augmented so as to inhibit any change in state of the desired joint, during movement of the manipulator to effect a commanded end effector movement.

In some embodiments, the system may be configured such that the velocities of the joints within the null-space are scaled according to the joint location and/or configuration, or any number of conditions. For example, a user may desire the proximal most joints be driven with a higher velocity than the more distal joints in the manipulator arm during reconfiguration movement. Additionally, the system may be configured so as to maintain a position or state of any one of the joints of the manipulator arm as desired.

In certain aspects, the system may receive the reconfiguration command from a system user in any number of ways. In some embodiments, the manipulator includes an input device for receiving a reconfiguration command from a user. The input device may include one or more buttons or mechanisms for driving one or more joints as desired (or alternatively for moving one or more links). The input device may be disposed on the manipulator arm, often at a location corresponding to the joint driven in response to activation of the device, such as described in U.S. application Ser. No. 13/906,767, entitled "Systems and Methods for Commanded Reconfiguration of a Surgical Manipulator Using the Null-Space," filed May 31, 2013, the entire contents of which are incorporated herein for all purposes. Alternatively, the system may include an input device having a cluster of buttons or mechanisms, each corresponding to a joint or linkage of the manipulator arm. This embodiment allows a user to reconfigure the arm from a centralized location. Alternatively, the input device may comprise a joystick that may be operated to drive one or more joints and effect reconfiguration as desired. It is appreciated that the input device may include any number of variations.

In another aspect, the Jacobian can be augmented by a coefficient (H) determined by a function that avoids collisions between adjacent manipulator arms and/or collisions between a manipulator arm and a patient surface. Such a function may achieve this desired movement in any number of ways, including determining a distance between corresponding points of adjacent manipulator or between a manipulator feature and a patient surface or determining a gradient field based on a relative positions of adjacent manipulators or a manipulator and a patient surface. In one example, the following equations may be used to effect collision avoidance by use of an augmented Jacobian.

$$y = H(q, \ldots)$$

$$\dot{x} = J\dot{q}$$

$$\begin{pmatrix} \dot{x} \\ \dot{y} \end{pmatrix} = \begin{pmatrix} J \\ dH/dq \end{pmatrix}\dot{q}$$

$$\dot{y} = dH\bigg/dq\begin{pmatrix} \text{joint states in} \\ \text{workspace} \end{pmatrix}\dot{q}$$

In the above equations, workspace calculations that provide the particular states of the manipulators within the workspace are included so that in combination with H (e.g. a desired relative relationship between corresponding points on adjacent manipulators or between manipulator and patient), collisions can be avoided. The following examples illustrate conceptually how such an augmentation may be applied to inhibit manipulator collisions.

In regard to inhibiting collisions between manipulators, in certain embodiments, such as shown for example in FIG. 5A, an example manipulator arm includes a proximal revolute joint J1 that rotates about a first joint axis so as to revolve the manipulator arm distal of the joint about the joint axis. In some embodiments, revolute joint J1 is mounted directly to the base, while in other embodiments, joint J1 may be mounted to one or more movable linkages or joints. The joints of the manipulator, in combination, have redundant degrees of freedom such that the joints of the manipulator arm can be driven through a range of differing configurations for a given end effector position. For example, the manipulator arm of FIGS. 5A-5D may be maneuvered into differing configurations while the distal member 511 (such as a cannula through which the tool 512 or instrument shaft extends) supported within the instrument holder 510 maintains a particular state and may include a given position or velocity of the end effector. Distal member 511 is typically a cannula through which the tool shaft 512 extends, and the instrument holder 510 is typically a carriage (shown as a brick-like structure that translates on a spar) to which the instrument attaches before extending through the cannula 511 into the body of the patient through the minimally invasive aperture.

Describing the individual links of manipulator arm 500 of FIGS. 5A-5D along with the axes of rotation of the joints connecting the links as illustrated in FIG. 5A-5D, a first link 504 extends distally from a pivotal joint J2 which pivots about its joint axis and is coupled to revolute joint J1 which rotates about its joint axis. Many of the remainder of the joints can be identified by their associated rotational axes, as shown in FIG. 5A. For example, a distal end of first link 504 is coupled to a proximal end of a second link 506 at a pivotal joint J3 that pivots about its pivotal axis, and a proximal end of a third link 508 is coupled to the distal end of the second link 506 at a pivotal joint J4 that pivots about its axis, as shown. The distal end of the third link 508 is coupled to instrument holder 510 at pivotal joint J5. The pivotal axes of each of joints J2, J3, J4, and J5 may be configured to be substantially parallel such that the linkages appear "stacked" when positioned next to one another, as shown in FIG. 5D, so as to provide a reduced width w of the manipulator arm and improve clearance around a portion of the manipulator during maneuvering of the manipulator assembly. In some embodiments, the instrument holder also includes additional joints, such as a prismatic joint J6, that facilitate axial movement of the instrument through the minimally invasive aperture and facilitate attachment of the instrument holder to a cannula through which the instrument is slidably inserted.

The cannula 511 may include additional degrees of freedom distal of instrument holder 510. Actuation of the degrees of freedom of the instrument may be driven by motors of the manipulator, and alternative embodiments may separate the instrument from the supporting manipulator structure at a quickly detachable instrument holder/instrument interface so that one or more joints shown here as being on the instrument are instead on the interface, or vice versa. In some embodiments, cannula 511 includes a rotational joint J7 (not shown) near or proximal of the insertion point of the tool tip or the remote center RC about which a shaft of the tool pivots adjacent a minimally invasive aperture. A distal wrist of the instrument allows pivotal motion of an end effector through cannula 511 about instrument joints axes of one or more joints at the instrument wrist. An angle between end effector jaw elements may be controlled independently of the end effector location and orientation.

Figure 5E:
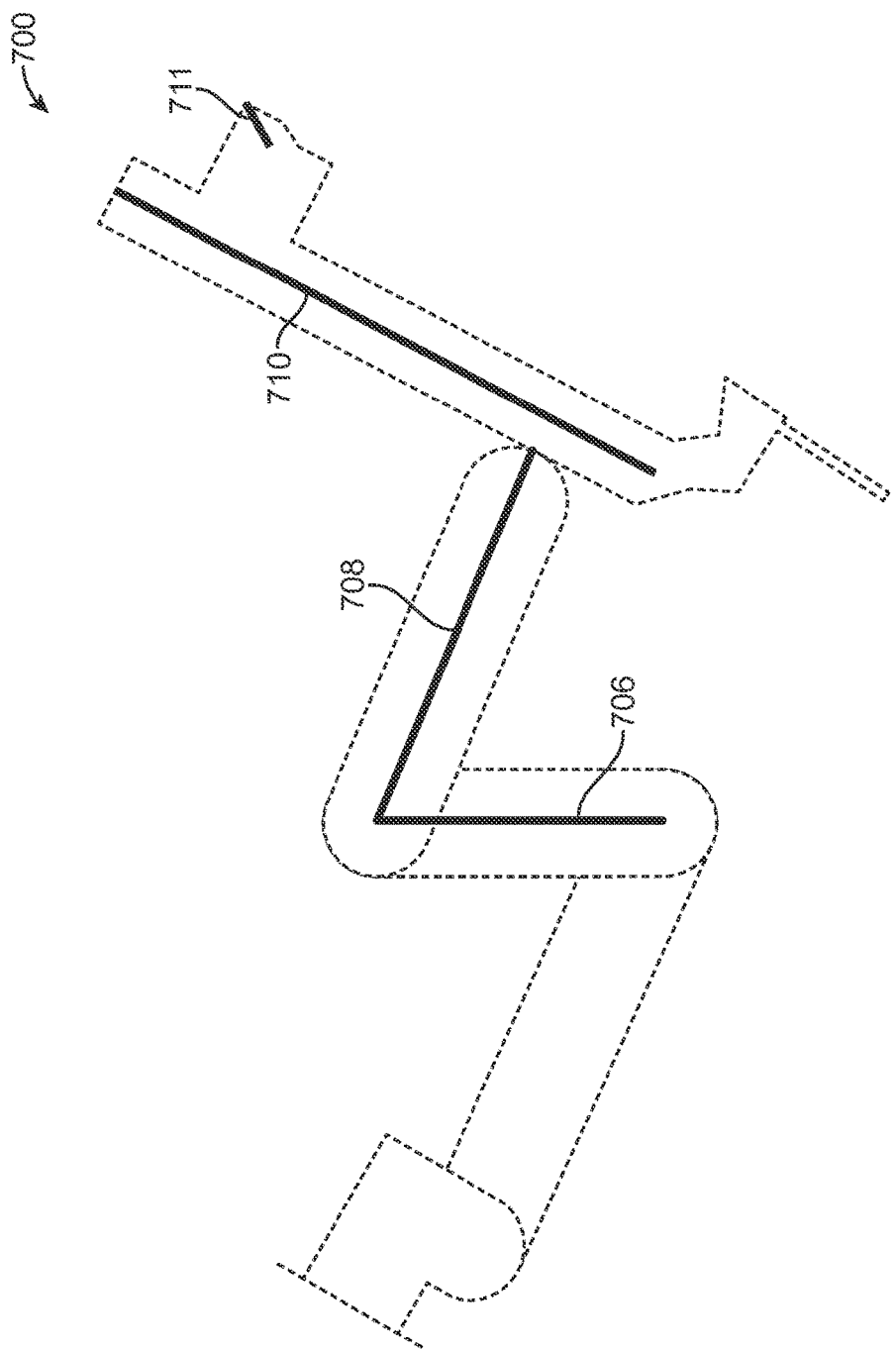
FIG. 5E shows a reference geometry including multiple line segments corresponding to components of the example manipulator arm shown in FIGS. 5A-5D.

In certain embodiments, the system uses a defined reference geometry corresponding to the position or state of each manipulator arm such that a processor of the system can determine when a collision between arms may be imminent by determining a relative state between reference geometries of adjacent manipulator arms. As shown in FIG. 5A, the reference geometry 700, sometimes called an "avoidance reference geometry", can include multiple line segments, 704, 706, 708, 701, 711 each corresponding to a linkage of the physical manipulator arm 500. The "reference geometry" itself is defined by the processor (or previously defined and/or input by a user) and its state is determined and tracked by the processor as the components of the manipulator move throughout a surgical space, typically using joint sensors. The line segments shown in FIG. 5A are for illustrative purposes to indicate how the reference geometry corresponds to the components or feature relating to the manipulator arm and to illustrate variations in how the reference geometry can be defined and utilized by the processor in accordance with the present invention to avoid arm-to-arm collisions. The reference geometry may further include points or line segments that correspond to protrusions or features relating to the manipulator arm, for example, line segment 711 corresponds to a protruding edge of a carriage movably mounted on the spar linkage 710 and line segment 712 corresponds to a protruding edge of the base of the instrument extending through cannula 511. As described herein, the reference geometry line segments defined which correspond to components of a first manipulator are collectively referred to as the "first reference geometry", such as shown in FIG. 5E, which graphically depicts reference geometry 700 as encompassing line segments 706, 708, 710, 711, and 712 that correspond to various components of manipulator arm 500.

Figure 16A:
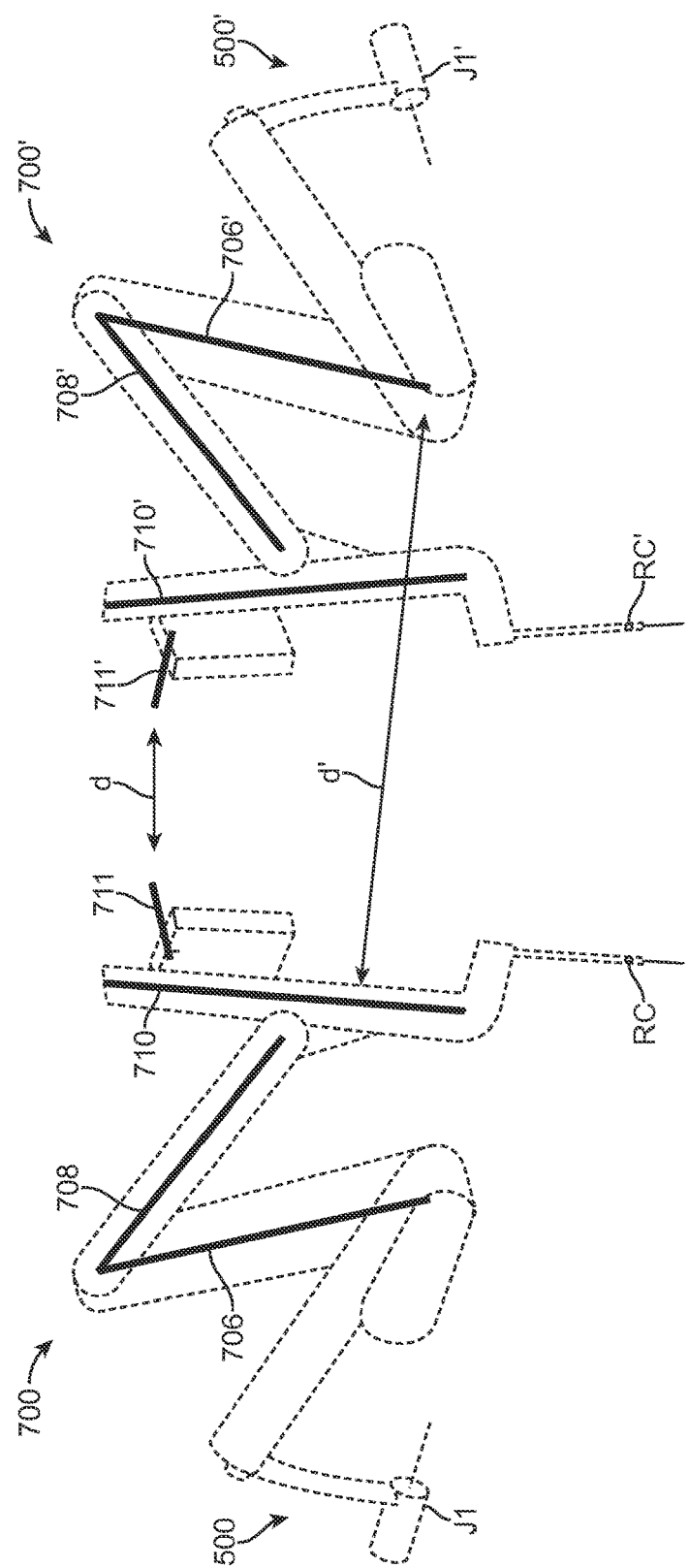
FIGS. 16A-16C illustrate interaction between a first reference geometry of a first example manipulator arm and a second reference geometry of a second example manipulator arm as used to calculate an avoidance movement for use in driving one or more joints to inhibit collisions between manipulator arms, in accordance with some embodiments.
Figure 16B:
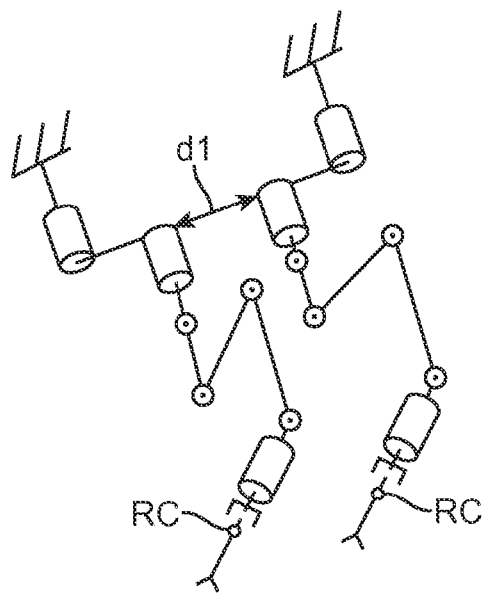
Figure 16C:
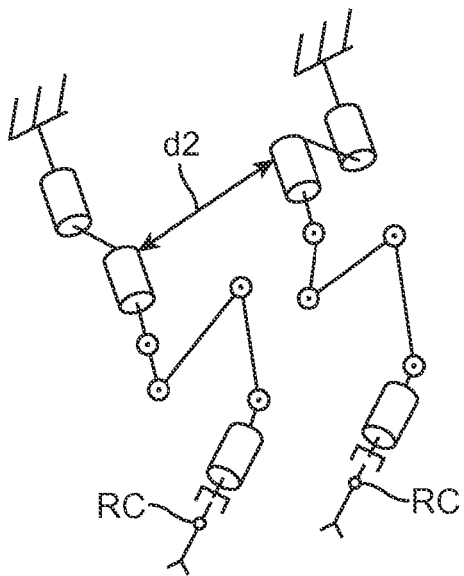

FIGS. 16A-16C illustrate an interaction of a first and second manipulator and an example use of a first and second avoidance reference geometry, as described above, in accordance with the present invention. The system in FIG. 16A includes a first manipulator 500 and a second manipulator 500', each having an identical assembly of joints linkages having a range of configurations for a given end effector position, although it is appreciated that various other manipulators could be used, as well as combining differing types of manipulators within the same system. In one aspect, the system calculates an avoidance movement of one or both manipulators by applying a virtual force between the line segments of reference geometry 700 and the line segments of reference geometry 700'. The processor uses the virtual force to calculate the joint forces that provide movement needed to move a pair of interacting elements away from one another. In some embodiments, the system may calculate a "repulsion force" between interacting elements of adjacent manipulators using the reference geometries described above along an avoidance vector extending between the interacting elements. The relative state, avoidance vector and repulsion force may be calculated in the three-dimensional workspace of the manipulator arms and then converted into joint space. The movement of the manipulator arm within the joint space is calculated using the kinematic Jacobian augments so that the resulting joint velocities increase separation between the reference geometries, which correspond to the manipulator structures themselves, while maintaining a desired position of a distal portion of the manipulators. Often, the force may be a function of the relative state or the distance between the reference geometries of each manipulator, a minimum or maximum distance, or a desired distance (e.g., $f(d > d\_max) = 0$, $f'(d) < 0$) (note: f' is the derivative of f). Use of a calculated repulsion force between interacting elements of the reference geometries for use in determining a vector or coefficient by which the Jacobian can be augmented so as to provide the desired separation between manipulators by avoidance movements within the null-space. The determination of functions/coefficients or calculation of avoidance vectors for use in augmenting the Jacobian.

In an example embodiment, the system determines at least a closest pair of elements from adjacent manipulators that could potentially interact or collide, often called "interacting elements." The pair of interacting elements, one from each manipulator, can include any pair of elements having a range of motion that overlaps. For example, in FIG. 16A, one interacting element pair is 711 and 711', while another interacting element pair is 710 and 706'. In some embodiments, the system only considers interacting element pairs within a specified separation distance. In response to a determination that a distance (d) between interacting element pairs is less than desired, such as the distance (d) between the interacting elements to which reference geometries 711 and 711' correspond, the processor calculates an avoidance movement of one or both manipulators to increase the distance between the interacting elements. In other embodiments, the calculation of avoidance movement may also include forces obtained using distances between other pairs of interacting elements, such as distance d' between 710 and 706' so as to provide more efficient movement or maintain a suitable distance between other interacting element pairs during movement. In certain embodiments, the avoidance movement is calculated by determining a repulsion force along a vector extending between the identified interaction elements or applying a virtual force in the work space of the manipulators and using this form to calculate the avoidance movement within the joint space.

In some embodiments, the avoidance movement is calculated so as to drive the joints of one manipulator of a pair used in the above calculations according to the calculated avoidance movement. In other embodiments, the avoidance movement may be calculated so as to drive one more particular joints of a manipulator, regardless of whether those joints are driven to effect other calculated movements. Additionally, avoidance movement may also be calculated to drive one or more particular joints of the manipulator arm, such as a joint that is not driven when effecting a displacing movement of the manipulator arm commanded by a user.

In the embodiment of FIG. 16A, in response to a determination that the distance (d) is less than desired, the processor determines calculated joint movements of the second manipulator 500' according to the kinematic Jacobian that is augmented so that the resulting joint movements increase the distance (d) between reference geometries 711 and 711'. As shown in FIG. 6A, the manipulator arms are each supported by a proximal revolute joint J1 that pivots the respective arm about an axis of the joint. As shown in FIGS. 16B-16C, movement of one or both manipulator arms using a combination of joints in one or both arms, respectively, can move an upper portion of the arm without changing the state of the end effector and its remote center RC. In FIG. 16B, the nearest points are determined by the system to be a distance (d1) apart. In response to this determination (or according to any of the methods described herein), the system drives one or more joints of one or both arms to increase the distance between nearest points (shown as d2 in FIG. 16C) without changing the state of the end effector at the end of each arm; thus, the system avoids a collision by augmenting the kinematic Jacobian so that one or more joints of the first and/or second manipulators maintain and/or increase a separate therebetween. In some embodiments, driving at least a first proximal joint may provide the avoidance movement while minimizing reconfiguration of a distal portion (e.g. end effector) of the manipulator, although a similar avoidance movement could be calculated to drive one or more joints of a more distal portion of the manipulator arm. In another aspect, the system may be configured to calculate the avoidance movement to move any of the joints described herein, whether or not such joints are driven when effecting displacing movement, or to include driving of joints according to hierarchy based on a particular configuration or state of the manipulator.

In accordance with certain embodiments, avoidance movement may be calculated according to a number of differing methods, which often include determining "nearest points" between manipulator arms. The nearest points can be determined either using calculations based on known manipulator positions or states via joint sensors or can be approximated using other suitable means, such as an external sensor, video, sonar, capacitive, or touch sensors, and the like. Embodiments may also use proximity sensors mounted on the driven linkages or slaves that can sense local arm-to-arm proximity and/or collisions.

In certain embodiments, the processor determines the nearest points on the line segments of each reference geometry. After applying the virtual repulsion force, the processor then calculates the repulsion force between the first and second manipulator. In one aspect, the reference geometry of each manipulator arm may be defined as "local line segments" such that interacting line segments on adjacent manipulator arms repel one another. In another aspect, the reference geometry of one manipulator may be defined as "local line segments" and the other as "obstacle line segments," such that only the local line segments are repelled by the virtual force. This aspect allows the system to avoid collisions by calculating an avoidance movement for only one or only some of the manipulator arms, thereby preventing unnecessary movement or overly complex avoidance movements. For example, in some embodiments, although the virtual force may be applied between line segments of each reference geometry, only the movement of the "local line segments" is calculated. In some embodiments, the processor converts the calculated forces obtained from applying the virtual force to joint velocities of the manipulator arms to be moved to according to the avoidance movement, which is then projected onto the null-space. By obtaining the virtual force that extends the joints and/or links of the manipulator within a null-space to maintain separation between manipulators, a coefficient or function can be determined by which the Jacobian can be augmented so that joint movements calculated therewith result in joint movements that inhibit collisions while maintaining the desired end effector state.

In an example embodiment, the processor determines a distance between at least one pair of reference geometry line segments from each manipulator arm, typically the nearest pair of line segments, often using a calculation within the work space of the manipulator arms. For line segment pairs that are closer than a certain maximum exclusion distance, the closest points are identified. The processor then applies a virtual repulsion vector, the strength of which is inversely proportional to the distance, which is then converted into the joint space and can be used to augment the Jacobian so that the calculated joint movements extend one or more joints within the null-space to maintain sufficient clearance between the line segments of the pair. The processor may perform the above process to more than one line segment pair. In such embodiments, the combined result of the repulsion vectors from all line segment pairs can be consolidated into a result or function of (H) (e.g. dH/dt) for use in augmenting the Jacobian, which may then be used by the joint controller to effect calculated movements that includes the avoidance movement within the null-space. These aspects are described in further detail below.

In another example embodiment, for each pair of manipulator arms, the processor first determines a pair of elements or components which could potentially contact or collide with one another using reference geometries corresponding to each elements, as described above. Using the corresponding reference geometries, the system then determines the closest elements of each pair, multiple interaction pairs, or a weighted sum of the effects of all element pairs, typically within a maximum exclusion distance. To calculate the avoidance movement, the processor generally first determines the nearest points on each pair of interaction elements and calculates an avoidance vector that may be used to "push" the elements away from each other. The avoidance vector may be calculated by generating a virtual force as described above and commanded a velocity in a direction to repel the elements from each other, or by various other methods. The processor then maps the forces needed to repel the elements away from each other at the nearest points of the reference geometries into an appropriate avoidance, which can then be used to augment the Jacobian and provide an avoidance movement within a null-space of the manipulator.

In one approach, the processor calculates an avoidance vector in a work space of the manipulator arms; transforms the avoidance vectors into the joint velocity space; and then projects the vectors onto the null-space using the result to obtain the avoidance movement. The processor may be configured to calculate a repulsion or avoidance vector between nearest points; map the avoidance vector into the motion of the "nearest" point of the manipulator arms, in the work space, and then determine a function of (H) by which to augment the Jacobian [Ken, please see comments in paragraph 0100.] that provide the desired direction and magnitude to move the nearest points away from one another. If multiple interacting points are used between various points or features on adjacent manipulator arms, the resulting null-space coefficients associated with the avoidance vectors from each interacting feature can be combined through summation.

In another approach, the processor may use a vector or a general term of the vector to accomplish as desired auxiliary task by means of an augmentation of the Jacobian. In one aspect, the processor may be configured to calculate a repulsion or avoidance vector between nearest points of the manipulator arms (e.g. avoidance geometries) for use in augmenting the Jacobian. If multiple features on the manipulator arms are used, the resulting joint vectors can be combined using various methodology.

In a first approach, the avoidance movement is determined by generating a potential field in joint-space, such that high potentials represent shorter distances between the manipulator arms and lower potentials represent larger distances. The H function is then determined by a function that descends down the negative gradient of the potential field, preferably to the greatest extent possible. In a second approach, the system determines a vector needed to avoid a collisions based on an avoidance geometry in the work space, and then determines the H by which to augment Jacobian that increases the distance between the avoidance geometries of the manipulator arms thereby increasing the distance between the nearest points on the manipulator arms.

In another aspect, movement of joints within the null-space provided by the augmented Jacobian may include an auxiliary task of inhibiting collisions between a manipulator and a patient surface. This may be accomplished by augmenting the Jacobian according to a function relating a distance between one or more features of the manipulator, such as a feature between the cannula holder, and a patient surface. This approach may utilize an avoidance geometry approximating the manipulator relative an obstacle surface approximating the patient surface.

Figure 17A:
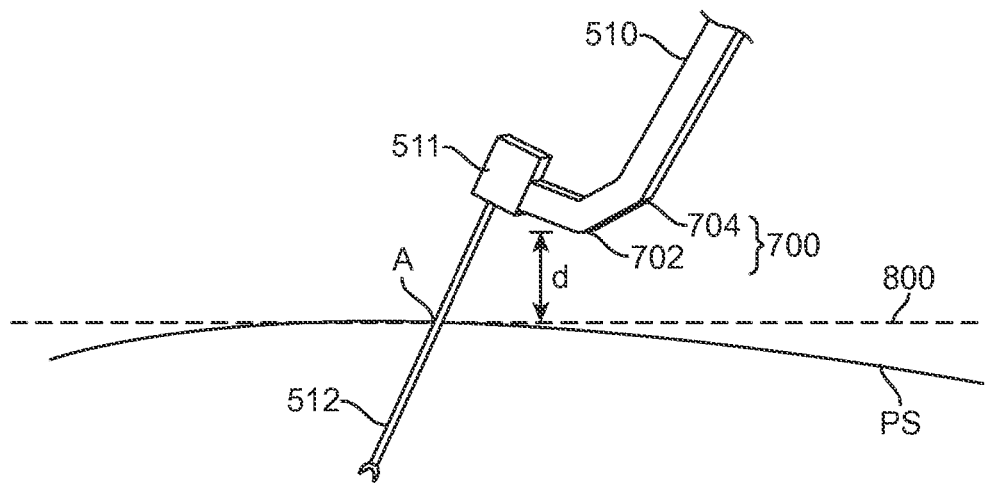
FIGS. 17A-17B show movement of the manipulator arm within a null-space and the associated distance between the avoidance geometry and obstacle surface.
Figure 17B:
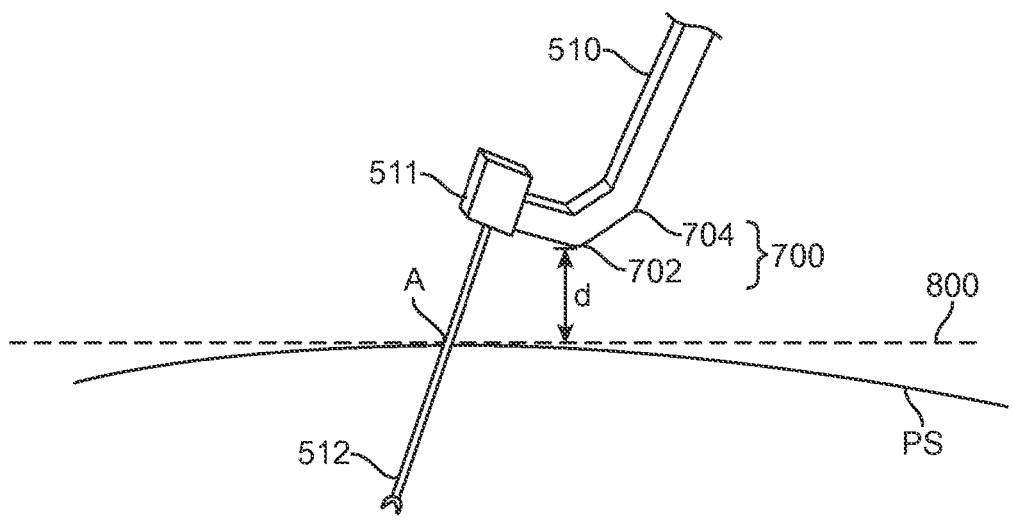

In the embodiment shown in FIGS. 17A and 17B, both an "avoidance geometry" of the manipulator arm and an "obstacle surface" corresponding to the outer patient surface is defined. In this embodiment, the location of the outer patient surface is roughly approximated by defining the obstacle surface 800 as a plane extending through the remote center, generally a horizontal plane. Since the instrument shaft of the tool pivots about the remote center which is adjacent the minimally invasive aperture it is assumed that the outer patient surface extends horizontally from the minimally invasive aperture; thus, the obstacle surface 800 most accurately represents the location of the outer patient surface at the remote center locations. The locations of the features of the manipulator arm are approximated by two reference points 702, 704, referred to collectively as avoidance geometry 700. The location and/or velocities of the avoidance geometry during commanded movement of the manipulator arm is generally determined using joint state sensors, from which the system can determine the shortest distance d between the avoidance geometry and the obstacle surface. In response to a determination that the distance d is less than desired, which may be indicative of a likely or potential arm-to-patient collision, the system augments the Jacobian in calculating the manipulator arm joint states so that the resulting joint movements calculated using the augmented Jacobian increase the distance d between the avoidance geometry 700 and the obstacle surface 800 when the joints are driven according to the calculated movement.

Figure 18:
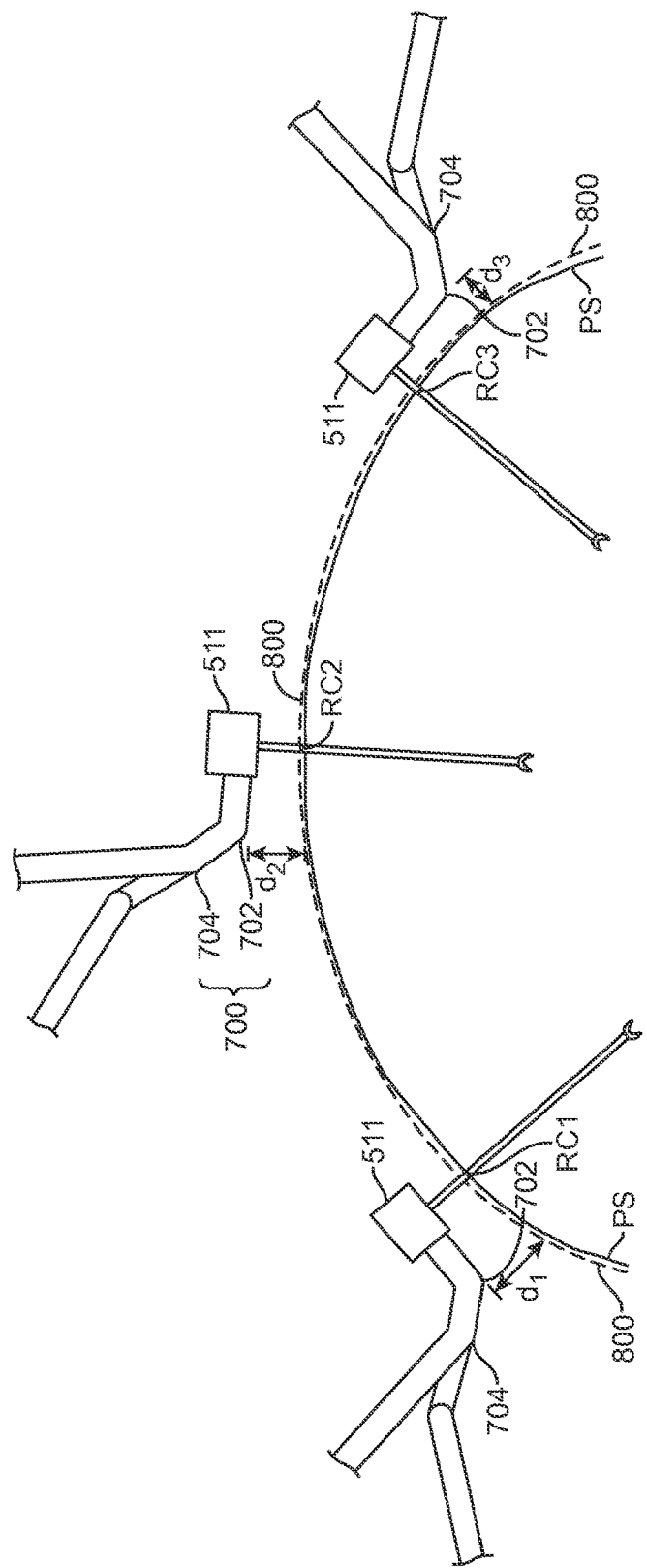
FIG. 18 shows an example system having multiple manipulator arms and an obstacle surface modeled so as to extend through the remote center of the each of the manipulator arms.

In the example embodiment of FIG. 18, the obstacle surface 800 is defined as a modeled surface that more closely approximates the outer surface of a typical patient. The obstacle surface 800 may be modeled in a variety of contours or shapes corresponding to the outer patient surface or may be modeled to incorporate positional data from a variety of sources, including a joint sensor, optical sensor, or ultrasound sensor. In some embodiments, the obstacle surface 800 is approximated by extending a modeled surface through two or more remote center locations, such as shown in the obstacle surface 800 of FIG. 18, which extends through three remote centers, RC1, RC2 and RC3, and approximates a cylindrical, spherical or convex shape more closely resembling an outer surface of a typical patient at the surgical site, such as a patient torso for example. By more accurately approximating the location of the outer patient surface, the system allows for an increased range of motion for each of the three manipulator arms, while still avoiding arm-to-patient collisions by driving the joints of the manipulator arms according to a calculated avoidance movement when the shortest distance between each of the manipulators, d1, d2, and d3, is less than desired.

In accordance with many embodiments, avoidance movement may be calculated according to a number of differing methods, which can include determining "nearest points" between the manipulator arm and the patient surface. The nearest points can be determined either using calculations based on knowing the manipulator positions or states via joint sensors or can be approximated using other suitable means, such as an external sensor, video, sonar, capacitive, a touch sensor, or the like.

In one approach, the processor calculates an avoidance vector in a work space of the manipulator arms; and then augments the Jacobian by an appropriate coefficient or function for use in augmenting the Jacobian so as to provide an avoidance movement that avoids collisions. The processor may be configured to calculate a repulsion or avoidance vector between nearest points; map the avoidance vector into the motion of the "nearest" point of the manipulator arm and the patient surface, in the work space, and then determine a function of (H) that provides the desired direction and magnitude to move the nearest points away from one another. In some aspects if multiple interacting points are used between various points or features on the manipulator arms and the patient surface, the resulting avoidance vectors from each interacting feature can be combined, such as by weighting or scaling, for use in augmentation of the Jacobian.

In another approach, the processor may be configured to calculate a repulsion or avoidance vector between nearest points of the manipulator arm and patient surface (e.g.

avoidance geometry and obstacle surface), and combine these with the avoidance vectors, so as to determine an appropriate coefficient by which to augment the Jacobian. If multiple features on the manipulator arms are used, the resulting joint velocity vector can be combined such as by weighting, scaling or other suitable methodology.

In one aspect, the avoidance movement may be calculated so as to include driving of any number of joints, or alternatively, to avoid driving particular joints of the manipulator arm. For example, in the manipulator arm shown in FIG. 5A, the avoidance movement could be calculated to include driving various combinations of joints J1, J2, J3, J4 and J5 (although in the depicted embodiment joints J3, J4 and J5 are included in a parallelogram arrangement and share the same state), or alternatively could be calculated to drive joint J6, as well as any other joints needed so as to move the manipulator arm within the null-space. Joint J6 of the manipulator arm illustrated in FIG. 8 may optionally be used as the joint coupling the instrument holder 510 to a distal link of the manipulator arm 508. Joint J6 allows the instrument holder 510 to twist or revolve about the axis of joint J6, the axis typically passing through the remote center or insertion point. Ideally, the joint axis is located distally on the arm and is therefore particularly well suited to moving the orientation of the insertion axis. The addition of this redundant axis allows the manipulator to assume multiple positions for any single instrument tip position, thereby allowing the instrument tip to follow the surgeon's commands while simultaneously avoiding collisions with the patient anatomy. The relationship between the axis of joint J6, the axis of J1 and the insertion axis of a tool tip extending through cannula 511 is shown in FIG. 9. FIGS. 10A-10C show the sequential twisting or pivotal movement of the cannula 511 about the joint axis as joint J6 shifts the insertion axis of the tool tip from side to side.

Figure 19A:
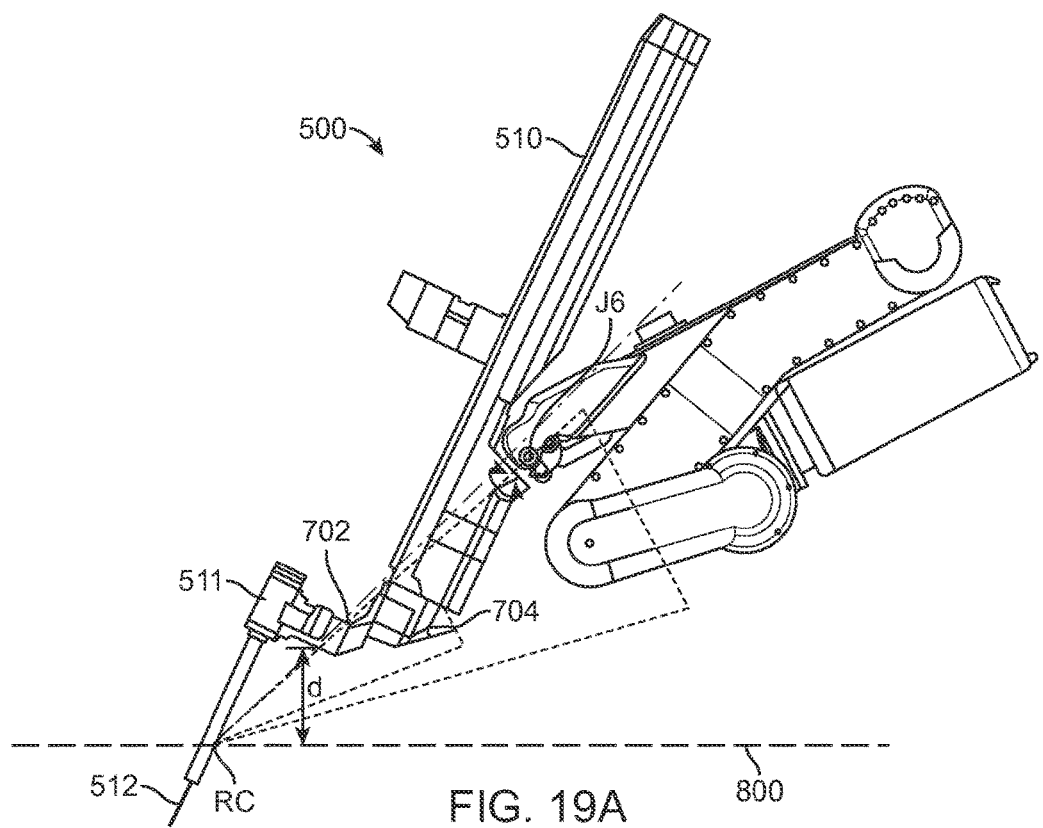
FIGS. 19A-19B show avoidance movement by driving of the distal revolute joint from an angular displacement of 0° to an angular displacement of 90°, respectively.
Commanded Reconfiguration (3770)
Figure 19B:
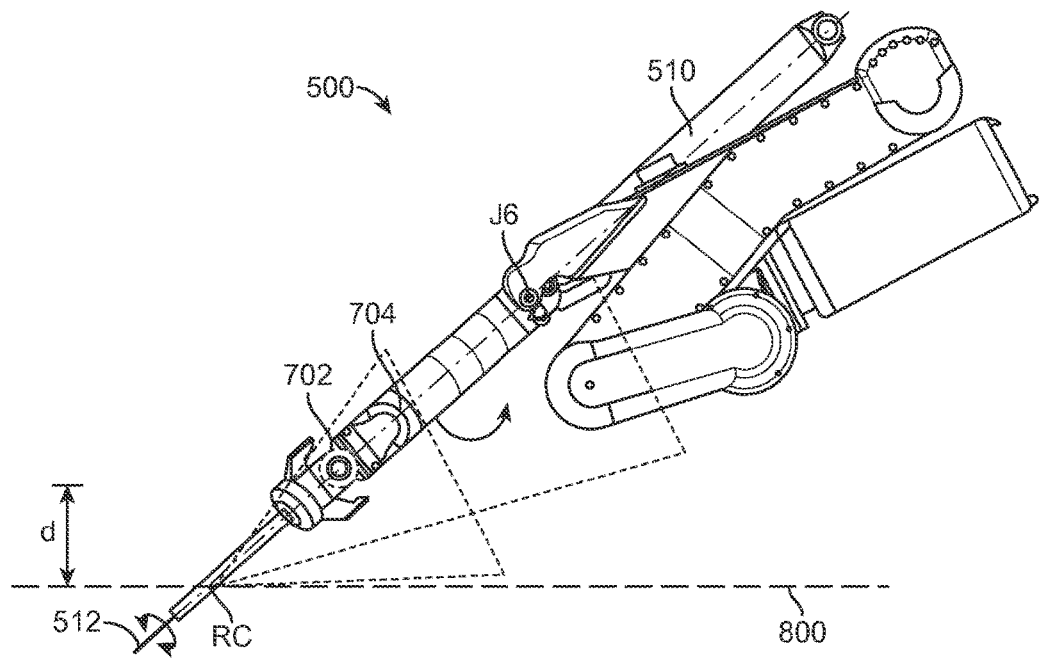

FIGS. 19A-19B illustrate one example of the use of joint J6 in accordance with the present invention. FIG. 19A illustrates the manipulator arm while the angular displacement of the joint J6 remains at 0°, at which the shortest distance between reference point 702 of avoidance geometry 700 and the obstacle surface 800 is distance d. In response to a determination that distance d is less than desired, the system calculates an augmented Jacobian for use in calculation of subsequent joint movements and drives joint J6 according to the subsequently calculated movement so as to twist or pivot cannula 511 and link 510 about the joint axis passing through the remote center RC about which cannula 511 pivots so as to increase distance d while maintaining the remote center of the instrument at a calculated pivotal center location. FIG. 19B illustrates the manipulator arm with the joint J6 having been driven to an angular displacement of 90° about its axis. As shown, the motion of the cannula 511 has increased the distance d between the nearest point 702 of the avoidance geometry and the obstacle surface 800. Thus, the described augmented Jacobian approach can be used to inhibit arm-to-patient collisions by including driving of a distal joint, such as joint J6.

Figure 20A:
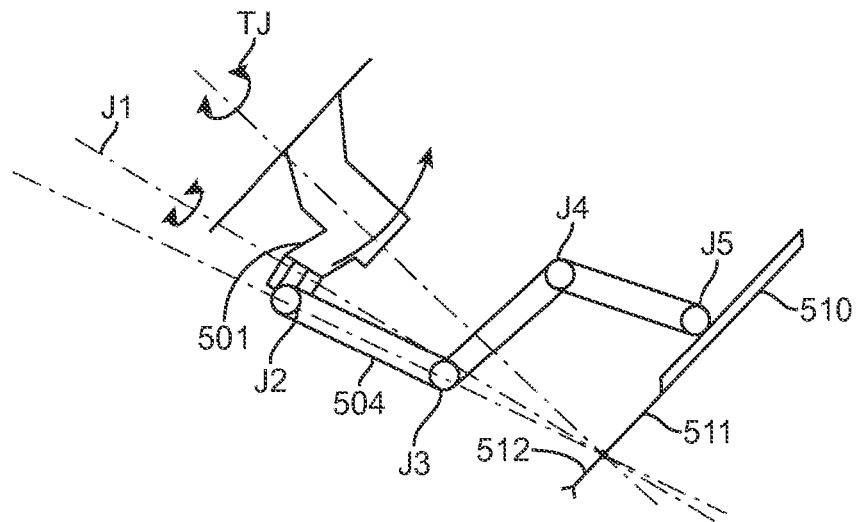
FIGS. 20A-20B illustrate reconfiguration of an example manipulator assembly for a given end effector position.
Figure 20B:
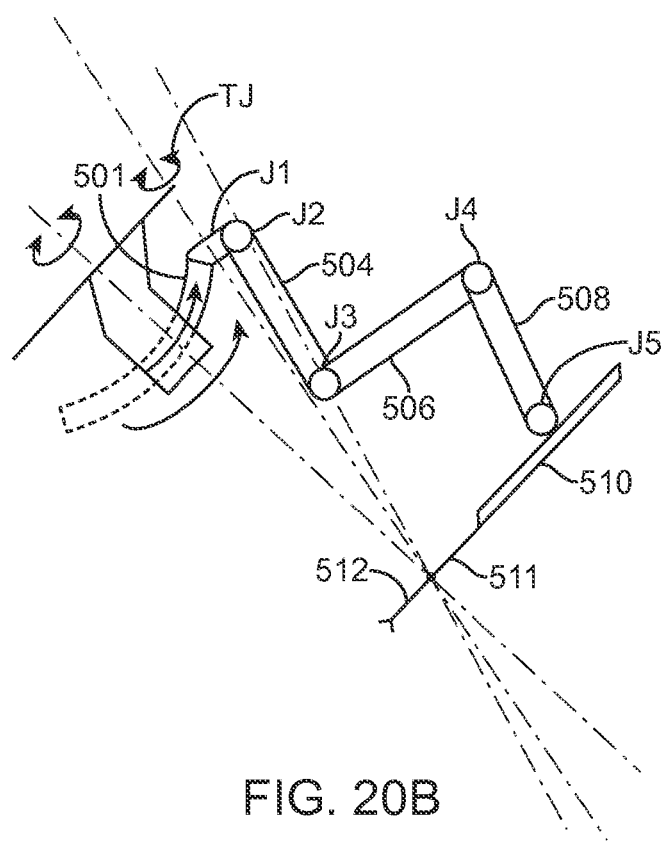
Figure 21A:
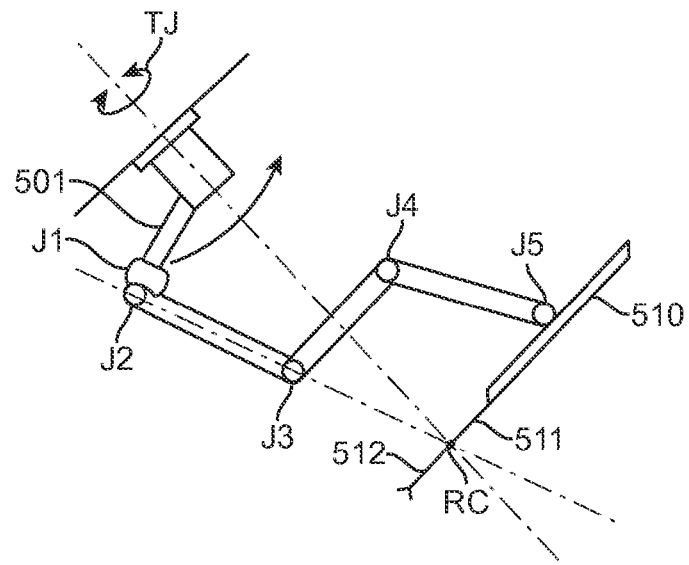
FIGS. 21A-21B illustrate an example manipulator for a given remote center location at which an associated instrument shaft pivots.
Figure 21B:
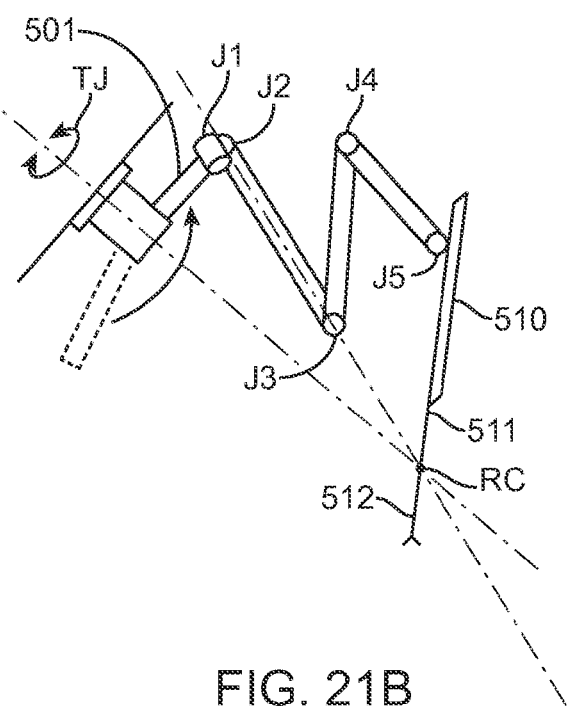

FIGS. 20A-20B schematically illustrate an example manipulator 500 before and after reconfiguring of the manipulator arm by driving the joints of the manipulator within the null space. In FIG. 20A, in response to a reconfiguration command entered by a user, the system drives the joint TJ counter-clockwise within the null-space for the given position of the end effector of instrument and according to the calculated movement of the remaining joints, the coordinated movements of the remaining joints within the null-space having been calculated by the system. In another aspect, the system may calculate the velocities of the joints with the kinematic Jacobian that is augmented so as to effect the desired configuration while the structural design of the manipulator arm maintains the remote center location, such as in the embodiment shown in FIGS. 21A-21B.

In some embodiments, the Jacobian is augmented so as to constrain movement of one or more joints for certain movements. For example, the Jacobian can be augmented so that one or more joints may be constrained during a commanded reconfiguration movement (e.g. displacement held at "0"), but allowed to move during various other types of movements as desired. In other embodiments, the system may augment the Jacobian so that the velocity of the joints driven within the null-space is limited or held at a substantially constant speed for a duration of the reconfiguration command. In still other embodiments, the system may augment the Jacobian so that the velocities of the joints within the null-space are scaled according to the joint location and/or configuration, or any number of conditions. For example, a user may desire the proximal most joints be driven with a higher velocity than the more distal joints in the manipulator arm during reconfiguration movement. Additionally, the system may augment the Jacobian to maintain a position or state of any one of the joints of the manipulator arm as desired.

Figure 22A:
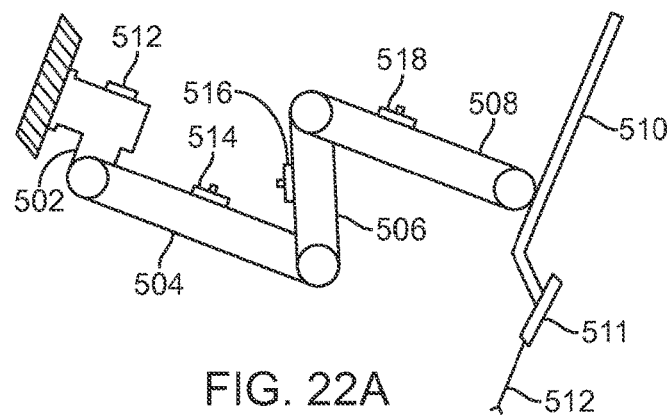
FIGS. 22A-22C illustrate three examples of manipulation command inputs in accordance with many embodiments.
Figure 22B:
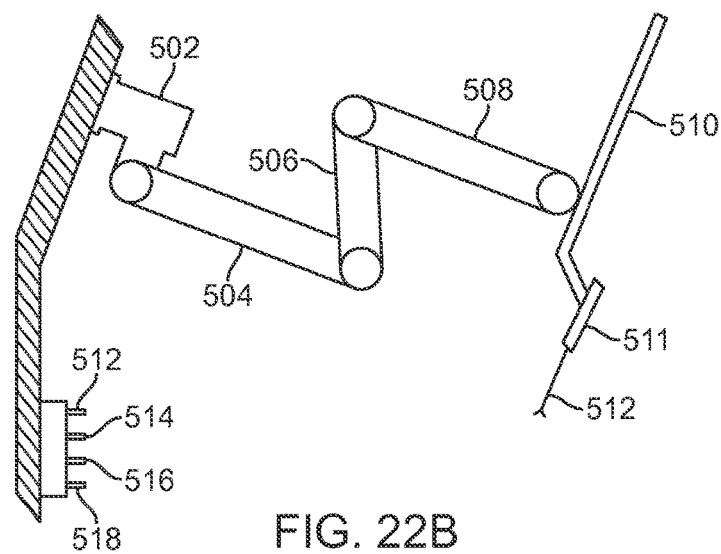
Figure 22C:
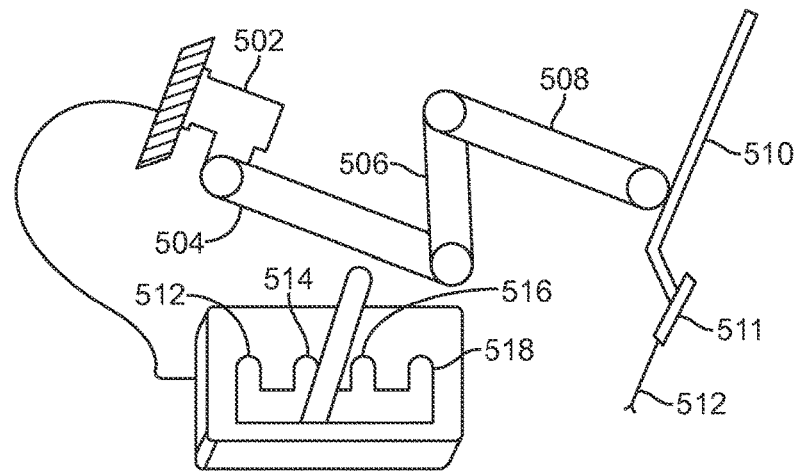

In another aspect, the system may receive the reconfiguration command from a system user in any number of ways. In certain embodiments, the manipulator includes an input device for receiving a reconfiguration command from a user. The input device may include one or more buttons or mechanisms for driving one or more joints as desired (or alternatively for moving one or more links) and may be disposed on the manipulator arm, preferably in a location corresponding to the joint driven in response to activation of the device, such as in FIG. 22A. Alternatively, the system may include an input device having a cluster of buttons or mechanisms, each corresponding to a joint or linkage of the manipulator arm, such as that shown in the embodiment of FIG. 22B. This embodiment allows a user to reconfigure the arm from a centralized location. The input device may also comprise a joystick, such as in FIG. 22C, that may be operated to drive one or more joints and effect reconfiguration as desired. It is appreciated that the input device may include any number of variations.

In another aspect, the Jacobian may be augmented so as to provide a desired emphases of one or more joints according to a particular direction or relative velocity. For example, in one example, the following equations may be used in order to emphases movement of a first joint (J5) relative another joint (J4) so that the joint velocity of J5 is maintained about twice that of the joint velocity of J4 during calculated movements of the manipulator.

$$\begin{pmatrix} \dot{x} \\ \dot{y} \end{pmatrix} = \begin{pmatrix} J \\ H \end{pmatrix} \dot{q}$$

$$\dot{y} = 0 \quad H = (0\ 0\ 1\ -1\ -2\ 0\ 0\ \dots)$$

$$\dot{x} = J\dot{q}$$

$$0 = \dot{q}_3 - \dot{q}_4 - 2\dot{q}_5$$

$$\dot{q}_3 - \dot{q}_4 + 2\dot{q}_5$$

In certain aspects, the system utilizes an augmented Jacobian that incorporates a potential function gradient and is applied to the Cartesian Space end effector velocities. The augmentation of the Jacobian calculates the joint velocities as desired. In accordance with the augmented Jacobian approach, the following equations may be used, although it is appreciated that column vectors may be used:

$$dx/dt = J * dq/dt$$

$$y = h(q)$$

$$dy/dt = \partial h/\partial q * dq/dt$$

$$[dx/dt^T dy/dt^T]^T = [J^T \partial h/\partial q^T]^T * dq/dt$$

$$d[x^T y^T]^T/dt = [J^T \partial h/\partial q^T]^T * dq/dt$$

$$dq/dt = [J^T \partial h/\partial q^T]^{T\#} d[x^T y^T]^T/dt$$

This approach may be illustrated in two examples, as follows:

In a first example: Set $dy/dt=0$, $\partial h/\partial q=[0\ 0\ 1\ -2\ 0\ 0\ 0]$, which tries to force the velocity of joint 3 to equal 2× velocity of joint 4.

In as second example: Set $dy/dt=0$, $\partial h/\partial q=[0\ 0\ 1\ 0\ 0\ 0\ 0]$, which tries to force the velocity of joint 3 to equal 0.

Figure 23A:
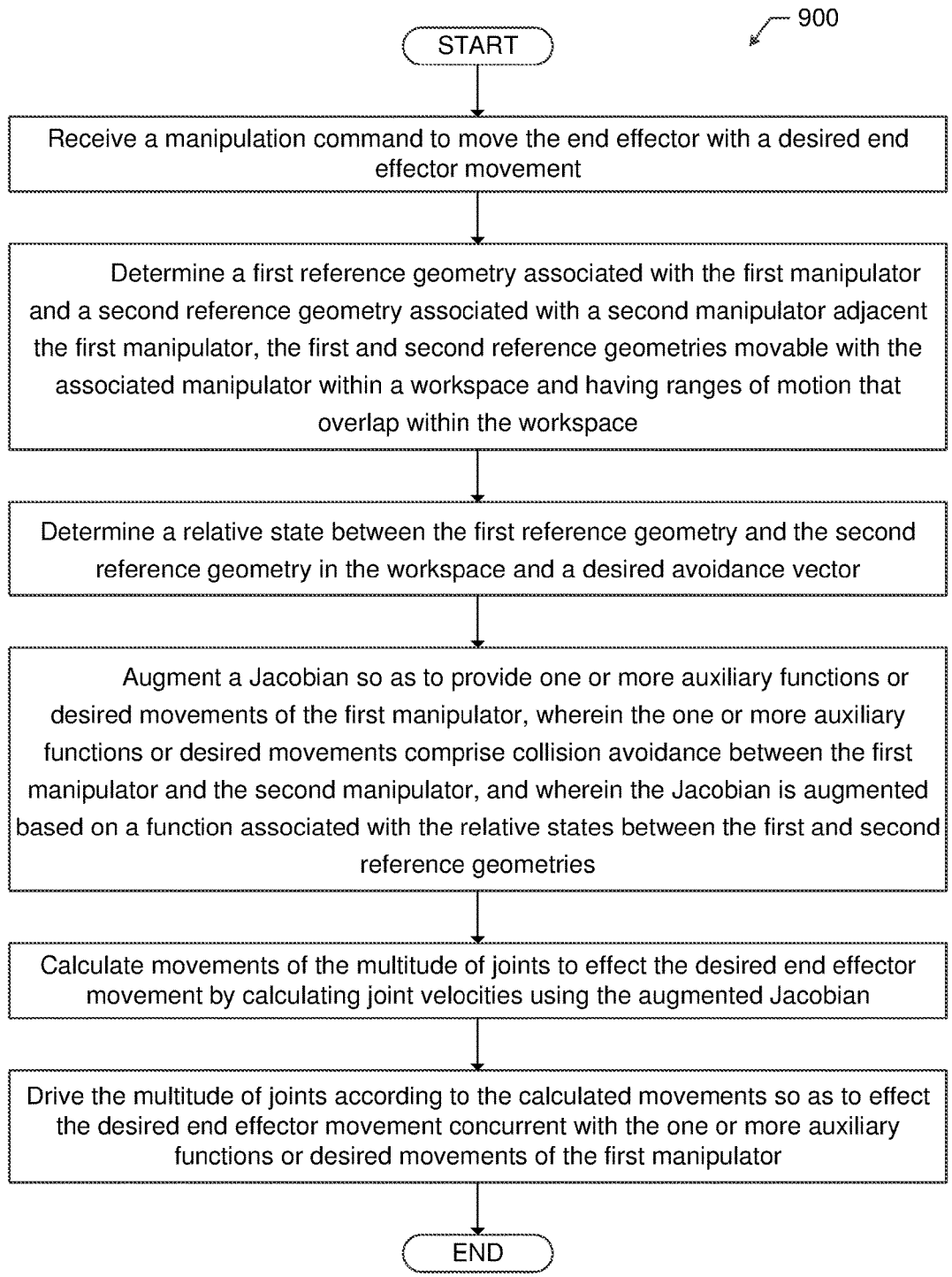
FIG. 23A and FIG. 23B show flowcharts in accordance with one or more embodiments.
Figure 23B:
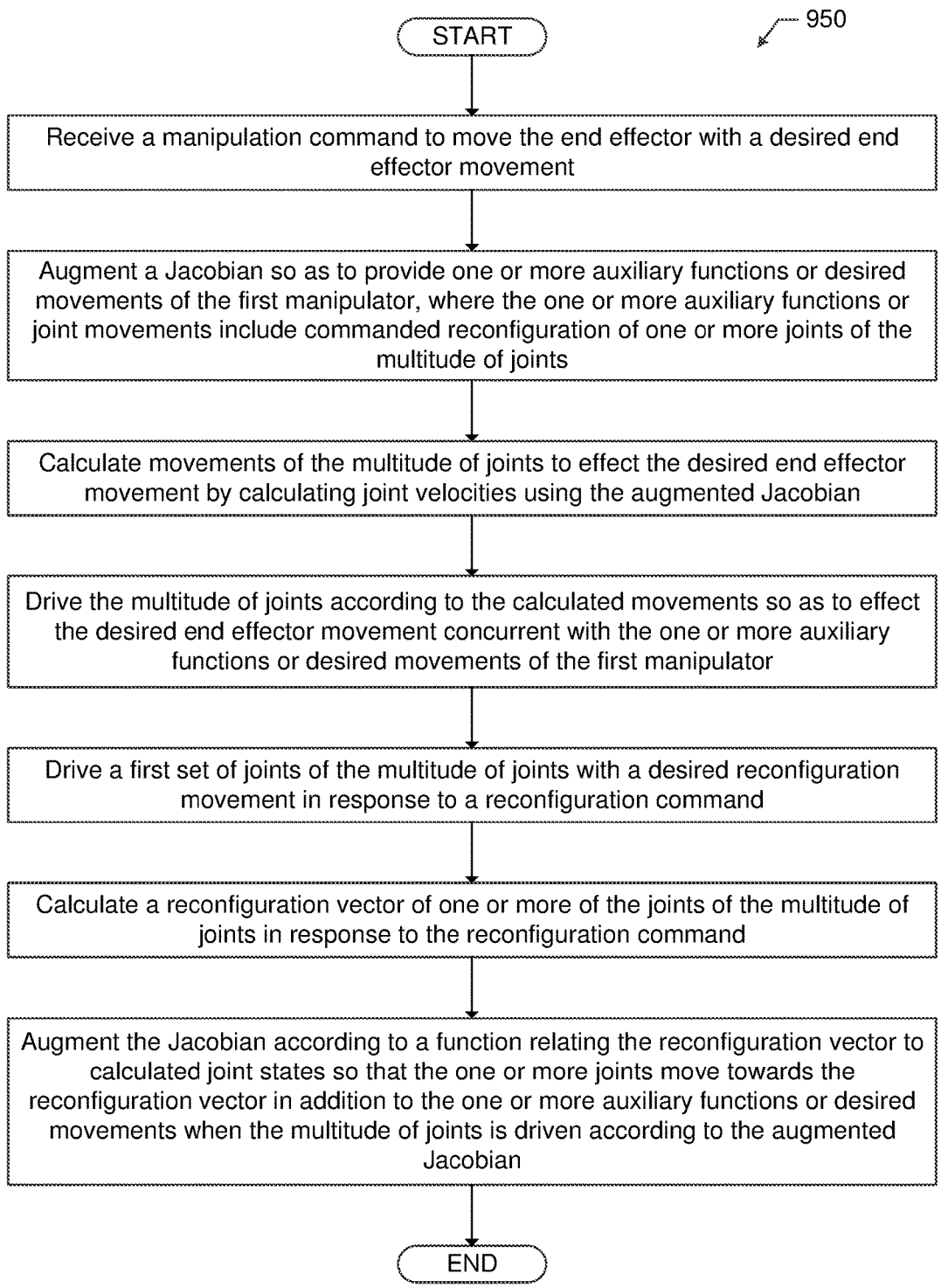

FIG. 23A shows a flowchart (900) in accordance with one or more embodiments. FIG. 23B shows a flowchart (950) in accordance with one or more embodiments.

While the example embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A robotic method for a system comprising a first manipulator, the first manipulator including: a movable distal end effector, a proximal portion coupled to a base, and a plurality of joints between the end effector and the base, the plurality of joints having sufficient degrees of freedom to allow a range of differing joint states for a given end effector state, the method comprising:
receiving a manipulation command to move the end effector with a desired end effector movement;
determining a first reference geometry associated with the first manipulator and a second reference geometry associated with a second manipulator adjacent the first manipulator, the first reference geometry movable with the first manipulator within a workspace, the second reference geometry movable with the second manipulator within the workspace, and the first and second reference geometries having ranges of motion that overlap within the workspace;
determining a relative state between the first reference geometry and the second reference geometry in the workspace and a desired avoidance vector;
augmenting a Jacobian so as to provide one or more auxiliary functions or desired movements of the first manipulator, wherein the one or more auxiliary functions or desired movements comprise collision avoidance between the first manipulator and the second manipulator, and wherein the Jacobian is augmented based on a function associated with the relative state between the first and second reference geometries;
calculating movements of the plurality of joints to effect the desired end effector movement by calculating joint velocities using the augmented Jacobian; and
driving the plurality of joints according to the calculated movements so as to effect the desired end effector movement concurrently with the one or more auxiliary functions or desired movements of the first manipulator.

2. The robotic method of claim 1, wherein the Jacobian is augmented according to a function associated with the one or more auxiliary functions or desired movements of the first manipulator.

3. The robotic method of claim 2, wherein the one or more auxiliary functions or desired movements of the first manipulator comprises the desired end effector movement, and wherein the Jacobian without augmentation is configured to pivot the first manipulator about a calculated pivotal center location, wherein the calculated pivotal center location is calculated so as to remain adjacent an aperture.

4. The robotic method of claim 1, wherein the one or more auxiliary functions or desired movements of the first manipulator comprise any of: commanded end effector movement, joint motion cancellation, collision avoidance between adjacent manipulators or between a manipulator and a patient, commanded reconfiguration of one or more joints of the plurality of joints of the first manipulator, a pitch-null float feature, facilitated access to edges of Cartesian-coordinate space, emphasizing joint motion anisotropically.

5. The robotic method of claim 1, wherein the Jacobian is augmented according to a function or limitation that avoids movement of a subset of joints of the plurality of joints that are desired to be non-moving joints such that driving the plurality of joints according to the calculated movements effects the desired end effector movement while inhibiting movement of the subset of joints.

6. The robotic method of claim 1, wherein the one or more auxiliary functions or desired movements comprise collision avoidance, wherein the Jacobian is augmented based on a function relating to a proximity of the first manipulator to the second manipulator adjacent the first manipulator so that collisions between the first and second manipulators are inhibited as compared to joint movements of the first and second manipulators calculated with the Jacobian without augmentation.

7. The robotic method of claim 1, wherein the one or more auxiliary functions or desired movements comprise collision avoidance between a feature of the first manipulator and a patient surface, wherein augmenting the Jacobian comprises:
determining a relative position between the feature of the first manipulator and the patient surface; and
determining an avoidance vector of one or more joints that corresponds to maintaining sufficient clearance between the feature of the first manipulator and the patient surface.

8. The robotic method of claim 7, further comprising:
determining an avoidance geometry corresponding to a movable position of the first manipulator; and
determining an obstacle surface corresponding to a position of a patient tissue surface, wherein the avoidance vector is calculated so as to maintain a desired relationship between the avoidance geometry and the obstacle surface.

9. A robotic method for a system comprising a first manipulator, the first manipulator including: a movable distal end effector, a proximal portion coupled to a base, and a plurality of joints between the end effector and the base, the plurality of joints having sufficient degrees of freedom to allow a range of differing joint states for a given end effector state, the method comprising:

receiving a manipulation command to move the end effector with a desired end effector movement;

augmenting a Jacobian so as to provide one or more auxiliary functions or desired movements of the first manipulator, wherein the one or more auxiliary functions or joint movements comprise commanded reconfiguration of one or more joints of the plurality of joints;

calculating movements of the plurality of joints to effect the desired end effector movement by calculating joint velocities using the augmented Jacobian;

driving the plurality of joints according to the calculated movements so as to effect the desired end effector movement concurrently with the one or more auxiliary functions or desired movements of the first manipulator;

driving a first set of joints of the plurality of joints with a desired reconfiguration movement in response to a reconfiguration command;

calculating a reconfiguration vector of one or more of the joints of the plurality of joints in response to the reconfiguration command; and augmenting the Jacobian according to a function relating the reconfiguration vector to calculated joint states so that the one or more joints move towards the reconfiguration vector in addition to the one or more auxiliary functions or desired movements when the plurality of joints is driven according to the augmented Jacobian.

10. The robotic method of claim 1, wherein the one or more auxiliary functions or desired movements comprise commanded reconfiguration of the first manipulator, the method further comprising:

receiving a reconfiguration command to move one or more joints of the plurality of joints according to a desired state;

wherein augmenting the Jacobian comprises augmenting the Jacobian so that the one or more joints correspond to the desired state and joint movements calculated according to the augmented Jacobian achieve the desired state of the one or more joints concurrent with the desired end effector movement in addition to the one or more auxiliary functions or desired movements.

11. A tele-surgical system comprising:

a first manipulator configured for tele-operatively moving a distal end effector relative to a proximal base, the first manipulator having a plurality of joints between the distal end effector and a proximal portion coupled to the proximal base, the joints providing sufficient degrees of freedom to allow a range of joint states for a given state of the distal end effector;

an input device for receiving a manipulation command to move the end effector with a desired end effector movement; and a processor coupling the input device to the first manipulator, the processor configured to:

determine a relative state between a first reference geometry associated with the first manipulator in a work space and a second reference geometry associated with a second manipulator in the work space, the second manipulator adjacent the first manipulator;

determine an avoidance vector that corresponds to a desired separation between the first and second reference geometries;

augment a Jacobian according to provide one or more auxiliary functions or desired movements of the first manipulator, wherein the one or more auxiliary functions or desired movements comprise collision avoidance between the first manipulator and the second manipulator, wherein the Jacobian is augmented based on the avoidance vector such that joint movements calculated using the augmented Jacobian moves the first manipulator and the second manipulator towards achieving or maintaining the desired separation between the first and second reference geometries in the work space;

calculate the joint movements of the plurality of joints in response to the manipulation command by calculating joint velocities based on the augmented Jacobian; and transmit a command to the first manipulator to drive the plurality of joints according to the calculated joint movements so as to effect the desired end effector movement concurrently with the one or more auxiliary functions or desired movements, wherein the plurality of joints are driven according to the calculated joint movements such that collisions between the first manipulator and the second manipulator are inhibited as compared to joint movements calculated using the Jacobian without augmentation.

12. The tele-surgical system of claim 11, wherein the processor is configured so that Jacobian is augmented according to a function or a state of one or more joints associated with the one or more auxiliary functions or desired movements of the first manipulator.

13. The tele-surgical system of claim 11, wherein the one or more auxiliary functions or desired movements of the first manipulator comprise pivoting an instrument of the end effector about a remote center, wherein the calculated joint movements are calculated so as to maintain the remote center at a calculated pivotal center location.

14. The tele-surgical system of claim 11, wherein the processor is configured such that the one or more auxiliary functions or desired movements of the first manipulator comprises any of: commanded end effector movement, joint motion cancellation, avoidance of joints limits or a singularity, collision avoidance between adjacent manipulators or between a manipulator and a patient, commanded reconfiguration of one or more joints of the plurality of joints of the first manipulator, a pitch-null float feature, facilitated access to edges of Cartesian-coordinate space, emphasizing joint motion anisotropically or any combination thereof.

15. The tele-surgical system of claim 14, wherein the one or more auxiliary functions or desired movements of the first manipulator comprise a plurality of differing auxiliary tasks or desired joint movements, and wherein the processor is further configured to:

combine or filter the plurality of differing auxiliary tasks or desired joint movements so that augmenting the Jacobian provides a desired movement that includes one or more of the plurality of differing auxiliary tasks or desired joint movements.

16. The tele-surgical system of claim 15, wherein the plurality of differing auxiliary tasks or desired joint movements is combined within the augmented Jacobian by weighting or scaling the plurality of differing auxiliary tasks or desired joint movements.

17. The tele-surgical system of claim 15, wherein the processor is further configured so as to combine or filter the plurality of differing auxiliary tasks or desired joint movements by, before augmenting the Jacobian, selecting one or more of the plurality of differing auxiliary tasks or desired joint movements according to a priority.

18. The tele-surgical system of claim 15, wherein the processor is further configured so as to combine or filter the plurality of differing auxiliary tasks or desired joint movements by, before augmenting the Jacobian, selecting one or more of the plurality of differing auxiliary tasks or desired joint movements based on a state of one or more joints of the plurality of joints.

19. The tele-surgical system of claim 11, wherein the one or more auxiliary functions or desired movements comprise inhibiting movement of one or more joints of the first manipulator desired to be non-moving joints, wherein the processor is further configured to:
augment the Jacobian so as to maintain a state of the one or more joints of the first manipulator such that movement of the one or more joints is inhibited during the calculated joint movements to effect the desired end effector movement.

20. The tele-surgical system of claim 11, wherein the processor is configured such that the one or more auxiliary functions or desired movements is based on an autonomous algorithm.

21. The tele-surgical system of claim 11, wherein the one or more auxiliary functions or desired movements comprise collision avoidance between a feature of the first manipulator and a patient surface, wherein the processor is further configured to:
determine a relative position between the feature of the first manipulator and the patient surface, wherein the Jacobian is augmented based on the relative position of the first manipulator to the patient surface.

22. The tele-surgical system of claim 21, wherein the processor is further configured to:
determine a second avoidance vector of one or more joints by use of the determined relative position, wherein the second avoidance vector corresponds to maintaining a predetermined clearance between the feature of the first manipulator and the patient surface sufficient to inhibit collisions during manipulator movement.

23. The tele-surgical system of claim 22, wherein the processor is further configured to:
determine an avoidance geometry corresponding to a movable position of the first manipulator; and
determine an obstacle surface corresponding to a position of a patient tissue surface, wherein the avoidance vector is calculated so as to maintain a desired relationship between the avoidance geometry and the obstacle surface.

24. The tele-surgical system of claim 23, wherein the plurality of joints is driven according to the joint movements in response to determining that the avoidance geometry is less than a desired minimum distance from the obstacle surface.

25. The tele-surgical system of claim 11, wherein the system further comprises:
a reconfiguration input device for receiving a reconfiguration command to move a first set of joints of the plurality of joints with a desired reconfiguration movement, wherein
the processor is further configured to drive the first set of joints according to the desired reconfiguration movement in response to the reconfiguration command; and wherein
the processor is configured to augment the Jacobian by including commanded states of the first set of joints such that driving the plurality of joints according to the joint movements calculated with the augmented Jacobian effects the one or more auxiliary functions or desired movements of the first manipulator concurrent with the desired end effector movement and reconfiguration of the first set of joints.

26. The tele-surgical system of claim 25, wherein the first set of joints comprises a subset of joints, wherein a first joint from the first set of joints couples the proximal portion to the base, the first joint comprising a revolute joint that supports a distal portion of the first manipulator such that joint movement of the revolute joint pivots the distal portion of the first manipulator about a pivotal axis of the revolute joint, wherein the pivotal axis extends from the revolute joint and through a remote center so that an insertion axis of the first manipulator moves along a distally tapered cone oriented towards the remote center.

27. The tele-surgical system of claim 11, wherein a distal portion of the first manipulator is coupled with an instrument holder configured to releasably support a surgical instrument having an elongate shaft extending distally to the end effector such that the elongate shaft pivots about a remote center during surgery, and wherein herein a plurality of the joints comprise remote spherical center joints disposed distally of the proximal portion and proximally of a distal portion of the first manipulator, wherein the remote spherical center joints are mechanically constrained so that articulation of the remote spherical center joints pivot the distal portion of the first manipulator about first, second, and third remote center axes, the first, second, and third remote center axes intersecting the remote center.

28. A non-transitory computer program product having embedded therein executable instructions for a method for a system comprising a first manipulator, the first manipulator including: a movable distal end effector, a proximal portion coupled to a base, and a plurality of joints between the end effector and the base, the plurality of joints having sufficient degrees of freedom to allow a range of differing joint states for a given end effector state, the method comprising:
receiving a manipulation command to move the end effector with a desired end effector movement;
augmenting a Jacobian so as to provide one or more auxiliary functions or desired movements of the first manipulator, wherein the one or more auxiliary functions or desired movements comprise commanded reconfiguration of one or more joints of the plurality of joints;
calculating movements of the plurality of joints to effect the desired end effector movement by calculating joint velocities using the augmented Jacobian;
driving the plurality of joints according to the calculated movements so as to effect the desired end effector movement concurrent with the one or more auxiliary functions or desired movements of the first manipulator;
driving a first set of joints of the plurality of joints with a desired reconfiguration movement in response to a reconfiguration command;
calculating a reconfiguration vector of one or more of the joints of the plurality of joints in response to the reconfiguration command; and
augmenting the Jacobian according to a function relating the reconfiguration vector to calculated joint states so that the one or more joints move towards the reconfiguration vector in addition to the one or more auxiliary functions or desired movements when the plurality of joints is driven according to the augmented Jacobian.

29. The non-transitory computer program product of claim 28, wherein the one or more auxiliary functions or desired movements of the first manipulator comprises the desired end effector movement, and wherein the Jacobian without augmentation is configured to pivot the first manipulator about a calculated pivotal center location, wherein the calculated pivotal center location is calculated so as to remain adjacent an aperture.

30. The non-transitory computer program product of claim 28, wherein the Jacobian is augmented according to a function or limitation that avoids movement of a subset of joints of the plurality of joints that are desired to be non-moving joints such that driving the plurality of joints according to the calculated movements effects the desired end effector movement while inhibiting movement of the subset of joints.

31. The non-transitory computer program product of claim 28, wherein the one or more auxiliary functions or desired movements comprise collision avoidance, wherein the Jacobian is augmented based on a function relating to a proximity of the first manipulator to a second manipulator adjacent the first manipulator so that collisions between the first and second manipulators are inhibited as compared to joint movements of the first and second manipulators calculated with the Jacobian without augmentation.

* * * * *